United States Patent [19]

Sargeant et al.

[11] Patent Number: 4,938,475

[45] Date of Patent: Jul. 3, 1990

[54] BICYCLE RACING TRAINING APPARATUS

[76] Inventors: Bruce A. Sargeant, 137 N. Cobblestone, Orange, Calif. 92669; Mark J. Hoffenberg, 24306 Bellerive Cir., Laguna Niguel, Calif. 92677; Rob Reasons, 25108 Marguerite, #B19, Mission Viejo, Calif. 92692; Robert A. Walpert, 1421 Rolling Hill Dr., Montery Park, Calif. 91754

[21] Appl. No.: 89,329

[22] Filed: Aug. 25, 1987

Related U.S. Application Data

[63] Continuation-in-part of Ser. No. 54,749, May 26, 1987.

[51] Int. Cl.$^5$ .............................................. A63B 21/00
[52] U.S. Cl. ................................ 272/73; 364/431.01; 324/160
[58] Field of Search ...................... 272/DIG. 6, 72, 69, 272/73, 129; 73/116, 379, 862; 364/431.01; 324/160; 340/52 R

[56] References Cited

U.S. PATENT DOCUMENTS 2,784,591  3/1957  Shoor .
3,486,242  12/1969  Aronson .

(List continued on next page.)

FOREIGN PATENT DOCUMENTS 2950605  6/1981  Fed. Rep. of Germany ........ 272/73
0017570  of 1899  United Kingdom .................. 272/73

OTHER PUBLICATIONS

W. Von Dobeln, *A Simple Bicycle Ergometer*.
F. Katch, W. McArdle, G. Peckar and J. Perrine, *Measuring Leg Face-Output Capacity With an Isokinetic Dynamometer-Bicycle Ergometer*, The Research Quarterly, V. 45 No. 1.
M. Firth, A Sport-Specific Training and Testing Device for Racing Cyclists, Ergonomics, V. 24, No. 7, 565-571 (1981).

(List continued on next page.)

*Primary Examiner*—Richard J. Apley
*Assistant Examiner*—S. R. Crow

[57] ABSTRACT

In an exercising apparatus for supporting a bicycle, a pivotally mounted member connects to a rear axle of the bike to constrain movement of the axle about the pivot point of the support member. A support roller, located on the horizontally opposite side of the rear axle as is the pivot point, cooperates with the support member to support the rear wheel. A flywheel and variable load means are connected to the roller to simulate the inertia and variable load experienced during the riding of a real bicycle. Preferably, a front fork support connects to the front fork of a bicycle and has an adjustable feature which can change the elevation of the bicycle frame. The front fork support is inclined and connected to this rear axle support member so that when a rider of a bicycle connected to the apparatus leans toward or shifts his weight toward the front fork support, the front fork support bends and the rear tire of the bicycle pivots toward the roller to maintain frictional contact between the tire and roller.

The frictional losses in the bicycle and exercise apparatus can be determined by determining the deceleration of a bicycle wheel connected to the apparatus, and calculating the losses from the equation Torque equals Inertia times angular acceleration. The variable load means can then compensate for the frictional losses. The efficiency of the variable load means is also determined, and compensation is made for the inefficiency. The rider can select a race course and a desired level of competition, with corresponding loads being determined and exerted on the rider. The position of the rider relative to a simulated pack of riders is displayed, and the loads exerted on the rider are varied with this relative position in order to simulate wind load variations. The pack performance is also randomly varied to simulate real race conditions.

The heart rate of the rider is monitored, and the load exerted on the rider is controlled to maintain the heart rate within predetermined limits.

11 Claims, 9 Drawing Sheets

U.S. PATENT DOCUMENTS

| | | |
|---|---|---|
| 3,511,097 | 5/1970 | Corwin . |
| 3,526,042 | 9/1970 | Nelson . |
| 3,643,943 | 2/1972 | Erwin, Jr. et al. . |
| 3,767,195 | 10/1973 | Dimick . |
| 3,845,756 | 11/1974 | Olsson ................... 272/DIG. 6 |
| 3,848,467 | 11/1974 | Flavell . |
| 3,869,121 | 3/1975 | Flavell . |
| 3,903,613 | 9/1975 | Bisberg . |
| 3,940,989 | 3/1976 | Engerstam . |
| 4,060,239 | 11/1977 | Pfleiderer et al. ............ 272/DIG. 6 |
| 4,112,928 | 9/1978 | Putsch . |
| 4,123,935 | 11/1978 | Maringer ............................ 73/116 |
| 4,133,550 | 1/1979 | Brown . |
| 4,169,371 | 10/1979 | Witschi et al. .................... 73/116 |
| 4,184,678 | 1/1980 | Flavell et al. . |
| 4,244,021 | 1/1981 | Chiles, III . |
| 4,261,562 | 4/1981 | Flavell . |
| 4,354,676 | 10/1982 | Ariel . |
| 4,358,105 | 11/1982 | Sweeney, Jr. . |
| 4,408,613 | 10/1983 | Relyer ................... 272/DIG. 6 |
| 4,441,705 | 4/1984 | Brown . |
| 4,452,445 | 6/1984 | Csekes . |
| 4,477,072 | 10/1984 | DeCloux . |
| 4,493,485 | 1/1985 | Jones . |
| 4,519,603 | 5/1985 | DeCloux . |
| 4,542,897 | 9/1985 | Melton et al. . |
| 4,556,216 | 12/1985 | Pitkanen . |
| 4,566,692 | 1/1986 | Brentham . |
| 4,569,518 | 2/1986 | Fulks . |
| 4,571,682 | 2/1986 | Silverman et al. . |
| 4,580,983 | 4/1986 | Cassini et al. . |
| 4,596,386 | 6/1986 | Sackl . |
| 4,613,129 | 9/1986 | Schroeder et al. . |
| 4,625,551 | 12/1986 | Carnielli . |
| 4,642,769 | 2/1987 | Petrofsky . |
| 4,645,459 | 2/1987 | Graf et al. . |
| 4,647,036 | 3/1987 | Huszczuk . |
| 4,660,828 | 4/1987 | Weiss . |

OTHER PUBLICATIONS

J. Brooke and M. Firth, *Handbook to the Ergowhell* (1971).

D. Giezendanner, P. Prampero and P. Cerreteloi, *A Programmable Electrically Braked Ergometer*.

M. Hoes, R. Binkhorst, A. Quyl and A. Vissers, *Measurement of Forces Exerted on Pedal and Crank During Work on a Bicycle Ergometer at Different Loads* (1968).

A. Weltman and J. Regan, *A Reliable Method for the Measurement of Constant Load Maximal Endurance Performance on the Bicycle Ergometer* (1982).

N. Miller and D. Ross, *The Design of Variable Ratio Chain Drives for Bicycle's and Ergometer's Application to a maximum Power Bicycle Drive* (1980).

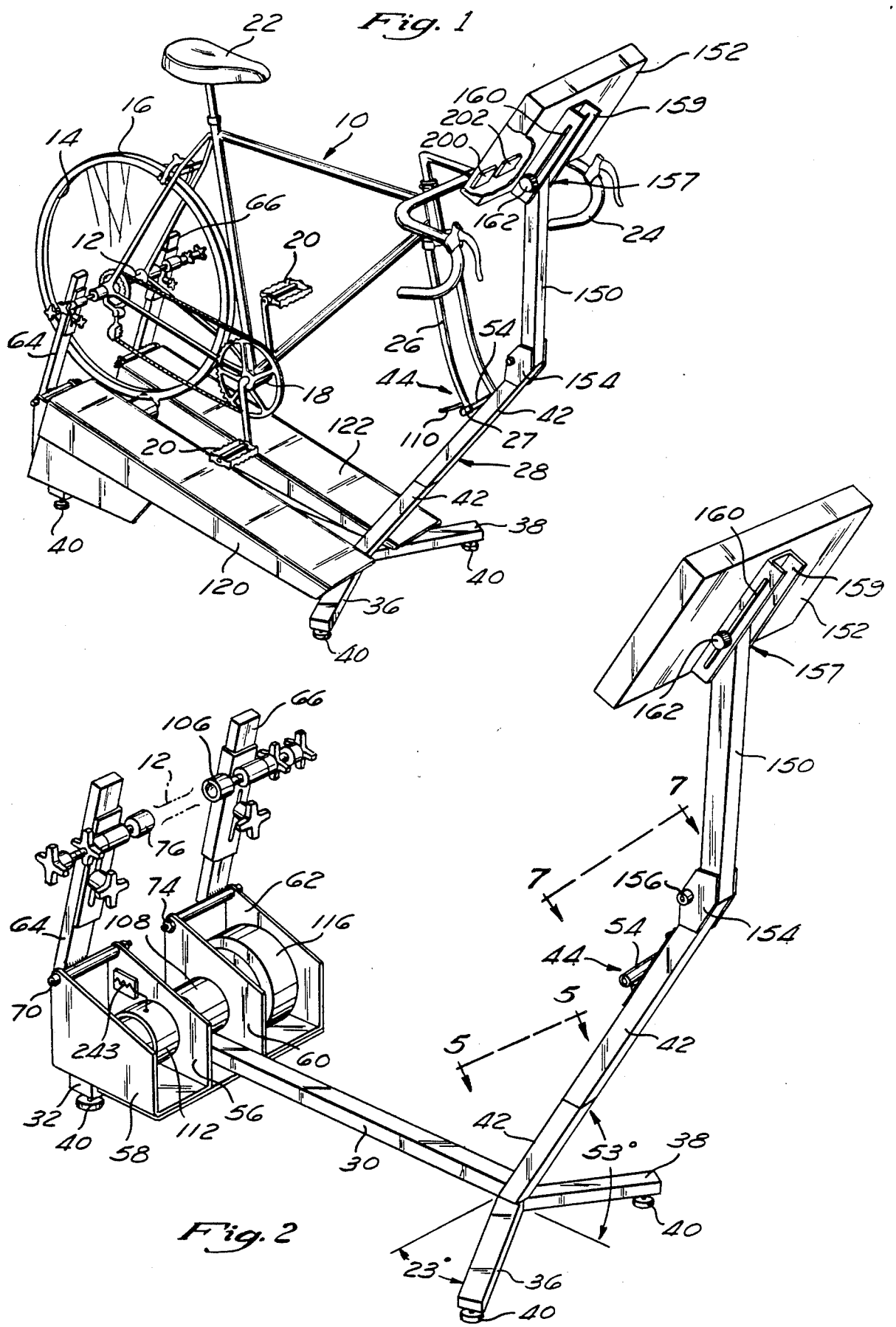

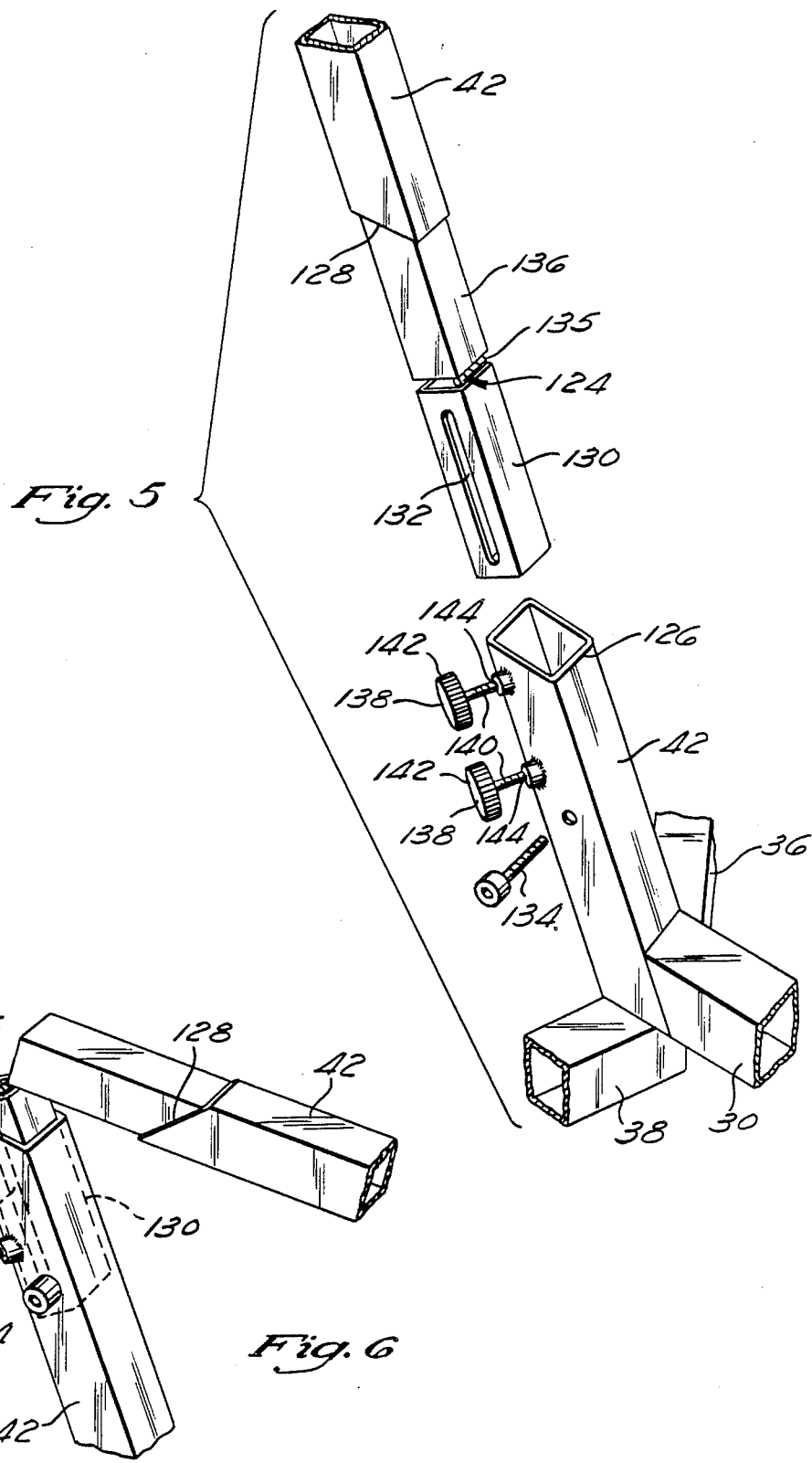

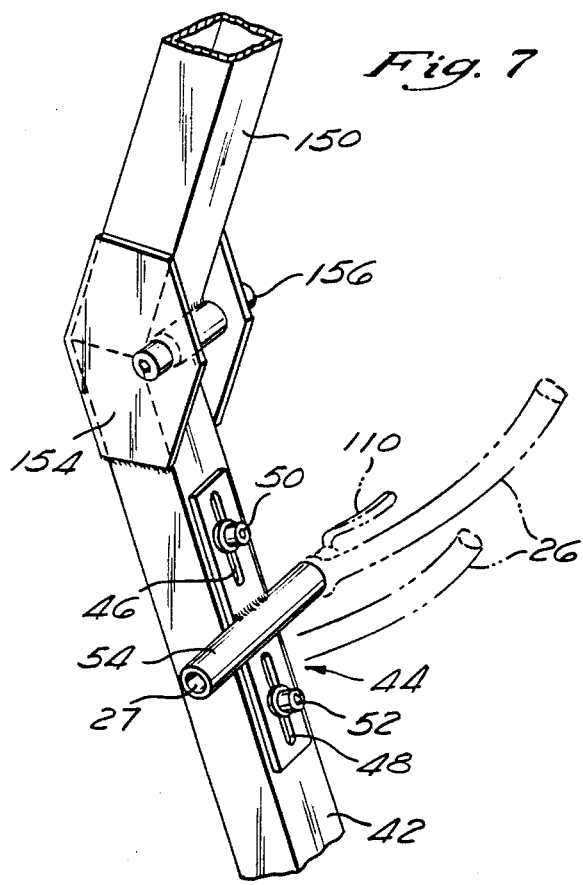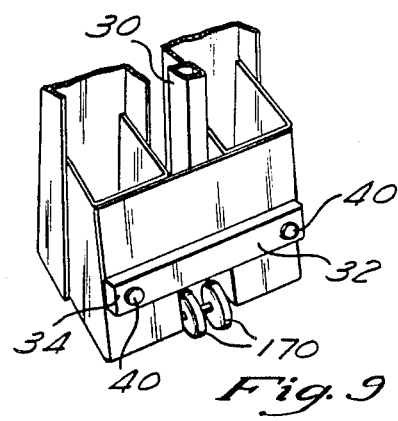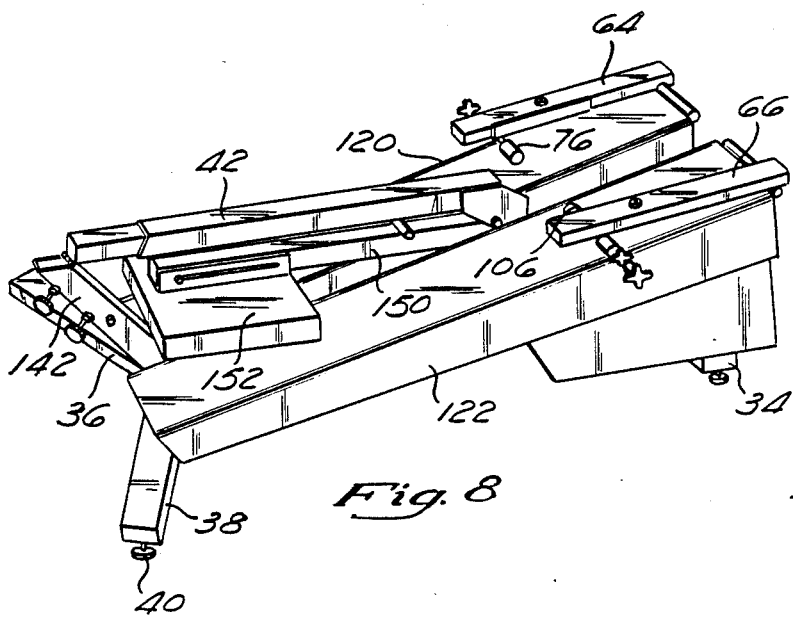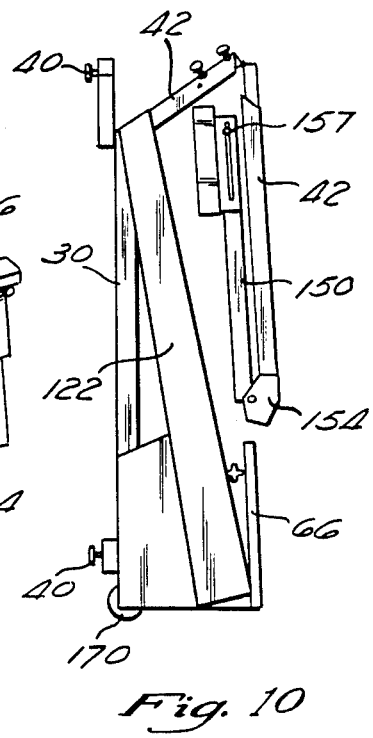

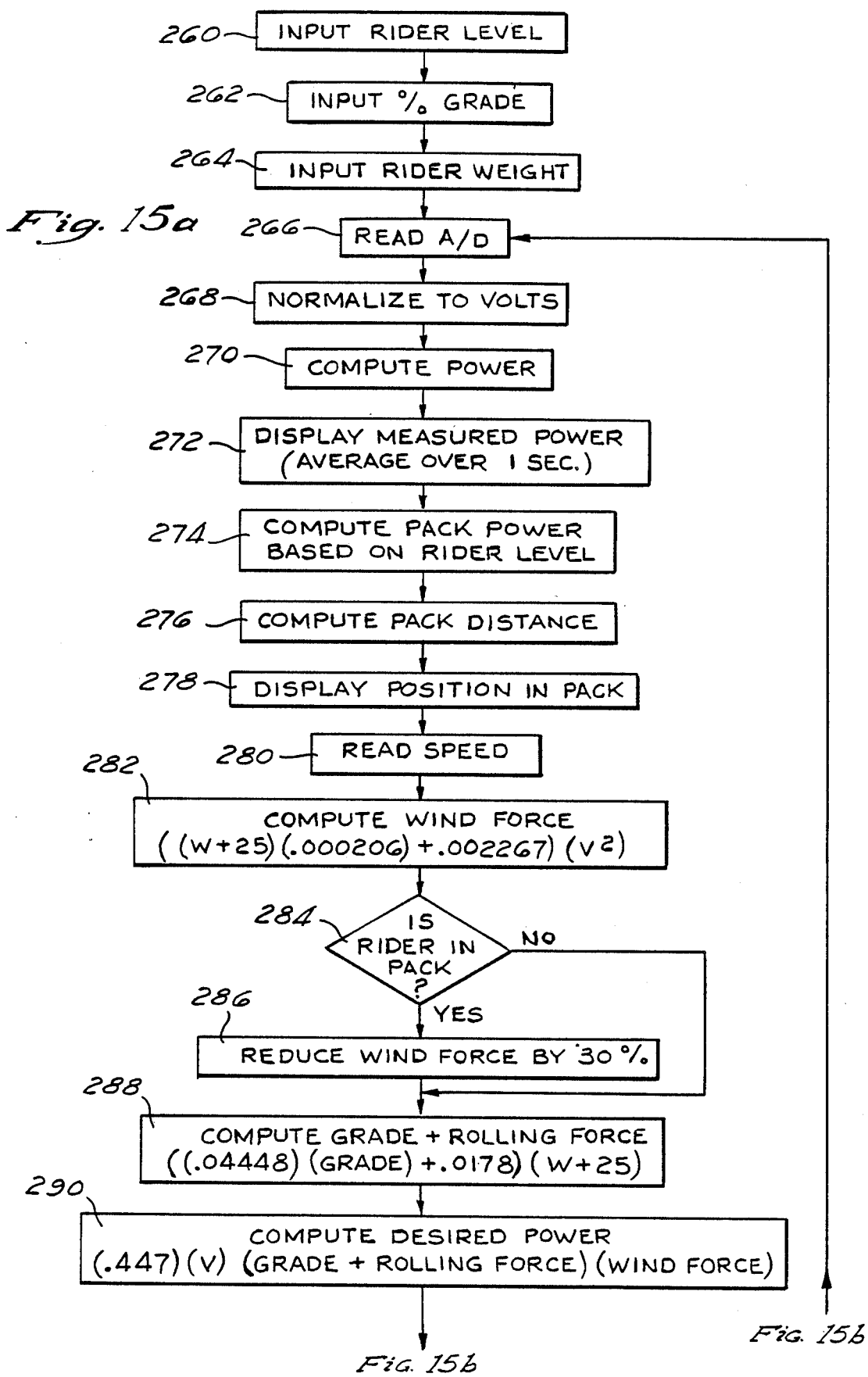

BICYCLE RACING TRAINING APPARATUS

This application is a continuation in part application of an application filed May 26, 1987, Ser. No. 054,749, by the same inventors.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

This invention generally relates to a bicycle-type stationary exercise apparatus used with load control devices, display devices, and heart monitoring devices. The invention is particularly directed to an apparatus for use with a multi-speed bicycle, and is especially suited to train for bicycle races.

FIELD OF THE INVENTION

A number of present-day gymnasiums and exercise clubs have stationary bicycle-type apparatus, whereby a person can pedal a simulated bicycle as a form of exercise. Typically, the bicycle pedals are connected to a frictional device or other load in a way such that the amount of resistance can be adjusted by the person riding the bicycle. Typical examples of this type of stationary bicycle are shown in U.S. Pat. Nos. 4,358,105 (the "Lifecycle") and 4,613,129.

Other exercise devices are adapted so that a conventional bicycle can be mounted to an apparatus which supports the bicycle so that the rear wheel of the bicycle can rotate against a frictional load. These types of devices fall into several general categories, the first of which connects both the front axle and the bottom bracket of the bicycle to a frame in order to support the bicycle. The rear wheel drives against a roller which, in turn, is connected to a loading mechanism. One example of such a device is shown in U.S. Pat. No. 4,441,705 to Brown, in which the rear wheel drives a flywheel and a variable resistance load.

A second type of apparatus used with a conventional bicycle supports the rear wheel, either on a pair of rollers or by a fixed support at the rear axle. For example, U.S. Pat. No. 4,596,386 to Sackl attaches to the rear axle to support the axle at a fixed distance from a pair of rollers. U.S. Pat. No. 3,903,613 to Bisberg supports the front wheel of the bicycle, while the rear wheel rests on a pair of rollers.

Each of the above types of devices has numerous drawbacks for use as an exercise device, and as use for a training device for bicycle racing. The stationary, simulated bicycles, like the "Lifecycle", do not provide a realistic pedal resistance simulating that obtained from riding a real bicycle; they do not adequately simulate inertia, wind resistance, terrain variations, and rolling resistance. Further, this type of stationary bicycle does not realistically simulate the body position or the feel of riding a bicycle, which is not surprising because a standard bicycle frame is not even used.

The devices using a bottom bracket support allow the use of a real bicycle frame, but fail to provide a realistic resistance and ride simulation. This type of equipment usually has one roller contacting the rear wheel.

The devices using a roller or rollers to support the rear wheel have stability and slippage problems. If the roller is behind the rear axle, the roller must be long since the wheel wobbles and moves sideways as it attempts to constantly "fall off" the roller. If the roller is in front of the axle, the wheel stays centered, but does not maintain adequate contact during periods of maximum torque on the rear wheel. In both cases, if a realistic resistance is applied, the rear tire slips on the roller.

For example, during some performance periods, the bicycle rider is not on the saddle, but is leaning over the handlebars and essentially standing on the pedals. As the weight of the rider shifts forward, the force on the rear wheel decreases and the weight on the front wheel increases, causing slipping of the rear wheel. Further, in this position with a bike on a bottom bracket support, the bicycle pivots about the bottom bracket, effectively removing the rear wheel from contact with the supporting roller or rollers. Thus, just when the maximum resistance is needed to prevent slipping at the rear wheel, the rear wheel is at a minimum friction contact with the resistance rollers and slips.

The rear wheel can be preloaded against the support roller(s), but the preload device duly constrains the rear wheel so as to ruin the realism of the ride, and also destroys the realism of the simulated resistance when the rider is sitting in the saddle or bicycle seat, pedalling at a slower speed. Further, the bottom bracket holds the frame too rigid, destroying the realism of the ride as in real life, the frame flexes on the wheels.

The devices which use a pair of support rollers on the rear wheel not only tend to be bulky, but require complicated resistance mechanisms on both rollers in an attempt to achieve an appropriate resistance to the rear wheel rotation. Further, they do not simulate the feel of a real ride and may require a different balance and training to be able to remain upright while riding if the front wheel is also supported on a roller, as in the patent to Cassini, et al., U.S. Pat. No. 4,580,983. For example, if the front fork is fixed or supported, with two rollers on the rear wheel, the rear wheel wobbles and moves while the front is stable. In real life, the rear wheel is stable while the front wheel wobbles or moves. The use of two rollers still does not prevent slipping when the rider comes out of the saddle and leans over the handlebars to exert the maximum force on the pedals. The shift in the rider's weight still causes slippage between the rear wheel and the rollers.

There is thus a need for a device which provides a realistic ride on a bicycle and a realistic resistance, especially so that slippage does not occur when the rider is standing on the pedals to obtain maximum power. Further, there is a need to make such a device portable, especially one which can be used with an individual's own bicycle to provide the maximum realism for training purposes.

Another aspect of this invention is the realistic simulation of the ride and load resistance experienced when riding a bicycle. The load variables can include wind resistance, whether the rider is going uphill or downhill, the inertia of the rider and bicycle, the friction inherent in the bicycle itself, and the frictional resistance between the bicycle tires and the riding surface.

Previous attempts to accurately replicate these various load effects have all had their drawbacks. For example, the effect of wind resistance has been simulated by rotating fan blades which are mechanically coupled to the rotational speed of the bicycle wheel. While the rotating fan blades can provide a force that increases as the square of the rotational speed of the fan blades, these fans are noisy, inaccurate, not readily adjustable, and cannot be adjusted to account for a variation in wind resistance that will occur with riders of different size and weight.

Similarly, prior devices have attempted to simulate the amount of load to be applied by either a mechanical or electronic brake system. A typical mechanical brake involves a friction belt that wraps around a moving surface to cause a frictional drag on that rotating surface depending upon the tension in the belt. These mechanical systems, however, cannot be accurately calibrated, have a slow response time, and are subject to load variations over time as the elements of the mechanical system go out of adjustment and alignment. The mechanical systems thus have poor repeatability, high variations in drag, and are difficult or impossible to accurately calibrate to a given load.

The electronic braking systems have advantages over the mechanical systems, but the accuracy of the simulated ride depends upon several factors, including how accurately the system can be calibrated, and the realism of the program with which the electronic brake is varied. An example of variations in the simulation accuracy would be the wind resistance. A fan blade may simulate a load that varies with the speed of the bicycle wheel, but it cannot simulate the load resistance that varies with the size and the weight of the rider, or the wind load variation that occurs from riding at the front of a pack, or in the middle of a pack of other bicycle riders. Thus, there is a need for a more realistic simulation of load variability, and especially the wind load variability.

Both electronic and mechanical braking systems are effective only if they are accurately calibrated, and if that calibration is maintained throughout the load simulation. Electronic systems have previously been calibrated by several methods, including the use of strain gauges, which are accurate, but very expensive and cumbersome to implement. Some electronic and mechanical systems will attempt to measure the system power output by the use of a device such as a generator, and then assume a constant system efficiency and friction in order to calibrate the system. This calibration system cannot accurately predict the frictional losses in the system or any variations in the friction or loads exerted on the bicycle and rider. This type of calibration system also has no absolute reference and is therefore difficult to use in predicting performance under variable conditions.

One final method of calibration is to select an absolute reference and measure system variations against that reference. This type of approach requires that the initial reference be accurately determined, that the reference not vary in real life under different load conditions, and that the reference can be used to accurately monitor and calibrate the various aspects of the system performance. One example of this type of system is an electronic brake which assumes that a specific voltage change will result in a known load variation. Several defects with this specific example are that the voltage and load relationship are difficult to predict and maintain over various temperatures and times, and that there is not a consistently accurate correlation between the voltage applied, and the load that the rider would realistically expect to experience in riding a real bicycle.

There is thus the need for a realistic way to calibrate the exercise system. There is a need for a realistic way to vary the loads in that exercise system so as to more accurately simulate the real life loads experience by a bicycle rider.

Yet another aspect of this invention is the ability to simulate realistic load conditions. U.S. Pat. No. 4,441,705 uses fans attached to a bicycle wheel to simulate wind load, while U.S. Pat. No. 4,542,897 to Melton shows a simulated competitor traveling at a predetermined speed. However, nothing in the prior art discloses varying the wind force according to the position of a racer with respect to one or more simulated riders. There is thus a need for a device which can simulate the race effect of varying the wind resistance depending on the position of the person exercising on the apparatus, with respect to a simulated rider.

Yet another aspect of this invention deals with the user's heart rate while exercising, which increases as the exercise progresses. To get the maximum benefit from the exercise, the heart rate should be within certain limits for a period of time. If the heart rate is too great, however, it is not productive, and may be damaging to the rider.

Prior devices, such as U.S. Pat. No. 3,767,195 to Delick, provide visual indicators to indicate an upper limit for the heart rate by flashing a visual indicator when the upper limit was reached. The rider determined how much, if at all, to decrease the exercise level in order to lower the heart rate.

There is thus a need for a device which monitors the user's heart rate and adjusts the applied load in order to maintain that heart rate, or to prevent exceeding maximum heart rate limits. Desirably, the device should provide optimum heart rates if the user does not know such information.

SUMMARY OF THE INVENTION

An apparatus is provided which supports a rear wheel and tire of a bicycle so that a forward shift in the rider's weight causes the rear tire of the bicycle to maintain frictional contact with a roller in order to prevent slippage. The roller is rotatably mounted about a first axis substantially parallel to a rear axle of a bicycle connected to the apparatus. The rear tire is constrained to move in a predetermined manner toward the roller. Preferably, the rear axle of the bicycle is supported on opposite ends of the axle shaft by axle clamps which are adjustably positioned on a rear axle support member. The support members constrains the rear axle to move along a predefined path which extends generally toward the roller. An arcuate path is preferred.

Preferably, the rear axle support means comprises a pair of members, each pivoted at one end about a pivot axis substantially parallel to the rotational axis of the rear wheel and tire. This pivot axis is preferably on the horizontally opposite side of the rear axle of the bicycle, as is the roller's rotational axis. The rear axle clamps can be adjustably positioned to accommodate different sizes of bicycles.

A variable load means, such as a motor, and preferably an alternator, and an inertial means, such as a flywheel, are connected to the roller and are preferably on a common shaft. The variable load and inertial loads exerted on the roller are transferred, via frictional contact with the rear tire, to the bicycle and its rider to simulate the momentum and load experienced during the actual riding of a bicycle. Such loads would include wind resistance, terrain variations, rolling resistance, and the inertia of the bike and rider.

While the roller and support member can be used alone to support the bicycle, it is preferred that the front fork of the bicycle is mounted to a front fork support tube by use of a fork mounting bracket. Preferably the front fork support tube is such that it provides a realistic flexibility to simulate a realistic ride. The fork mounting bracket is positionally adjustable to accommodate different sizes of bicycles. The mounting bracket can flex to simulate real life flexing of the fork and front wheel. By repositioning the mounting bracket relative to the front fork, the elevation of the attached bicycle frame can be changed to tilt slightly upward from a level orientation.

Preferably, the front fork support tube is connected to the same structure that supports the roller and rear axle support mount. Thus, a shift in the weight of the rider off of a bicycle seat toward the front fork will cause the front fork support tube to bend and cause the rear axle support mount to rotate the rear bicycle tire toward the roller so as to prevent slippage between the roller and rear tire.

The front fork support tube also supports a display which is in electronic communication with the roller and alternator so that data, such as the bicycle speed, can be displayed for viewing by the rider.

There is thus advantageously provided a means for supporting a bicycle so as to simulate a realistic ride on that bicycle while preventing slippage of the rear wheel of the bicycle during periods of maximum force on the pedals. The realistic ride includes the feel of the load on the rear tire, as well as the flexibility of the bicycle.

The exercise apparatus can be collapsed into a smaller, portable configuration for portability and for storage. The front fork support tube contains hinges which allow the tube to be folded into an adjacent relationship with the remainder of the apparatus. A releasable hinge adjacent the display unit, and a second releasable hinge located above the fork tube mount bracket, allows the display unit to be folded against the front fork support tube. The hinge at the bottom of the front fork support tube allows that tube, along with the display unit and its support members, to be folded into a position adjacent the roller. The pivot axes, about which the rear axle support members pivot, are positioned so that the rear axle support members can be folded into a position adjacent the roller. Wheels are provided on the end of the frame, adjacent the heavy flywheel and alternator, to allow easy movement of the portable package. There is thus provided a hinging means by which the apparatus can be folded into an adjacent relationship to present a smaller configuration which is much more portable than the operational configuration of the apparatus.

The apparatus is preferably calibrated to accurately produce the intended loads. One way to do this is to determine and compensate for the frictional losses in the apparatus when a bicycle is mounted on the apparatus. The steps for, such a calibration sequence comprise: rotating a wheel in an exercising device until the wheel attains at least a first predetermined rotational velocity; allowing the wheel to coast down to a second predetermined rotational velocity during which coasting period the loading device is not exerting loads on the wheel other than inherent frictional loads; sensing and recording the time and rotational velocity at periodic intervals as the wheel coasts down from the first velocity to the second velocity; determining the rotational mass moment of inertia of any components of the exercise device that rotate because the wheel rotates; performing a linear regression analysis on the recorded velocities and times to determine the deceleration of the wheel and rotating components as a function of velocity; and deriving the frictional load from rotation of the wheel and the rotating components of the exercise device from the formula Frictional torque equals the Mass Inertia times the Angular deceleration. An additional step would comprise computing the power required to overcome the frictional load from the formula: Power equals Mass moment times angular velocity.

The inefficiency of the loading device (which is preferably an alternator) is compensated for by the steps comprising: determining the efficiency of the loading device; determining the power output of the loading device by comparing the efficiency of the loading device with a second loading device for which the power output is known; and adjusting the loading device to account for the frictional losses and the efficiency of the loading device. Preferably, the efficiency is determined by performing a linear regression analysis to determine the power dissipated by the loading device at a predetermined speed, and by performing a linear regression analysis to determine the power which the loading device applies to the wheel.

When the loading device comprises an electrical device which exerts a load on the wheel where the load can be varied by varying the voltage applied to the loading device, the power dissipated is determined by the steps comprising: rotating the wheel until the wheel attains at least a third predetermined rotational velocity; allowing the wheel to decelerate to a fourth predetermined rotational velocity; applying a constant decelerating force from the electrical device in order to further decelerate the wheel as it decelerates from the third to the fourth velocities; sensing and recording the rotational velocity of the wheel and the voltage output by the electrical device at periodic intervals of time as the wheel decelerates from the third velocity to the forth velocity; performing a linear regression analysis on the recorded wheel velocity and the square of the voltage from the coast down between the third and fourth velocities to determine the deceleration of the wheel and rotating components as a function of velocity; and wherein the power output by the loading device is further determined by the step comprising: performing a linear regression analysis on the velocity and on the deceleration times the velocity from the coast down between the third and fourth velocities in order to obtain linear regression constants for use in determining the power applied.

When the calibration steps are implemented by the above described exercise apparatus, the above apparatus further comprises variable load-applying means communicating with the roller for applying variable loads to the roller to simulate variations in the load encountered during actual riding of a bicycle; and calibration means for determining the friction retarding the wheel from rotating so the variable load-applying means can compensate for the friction. Preferably the calibrating means further comprises means for determining the efficiency of the variable load-applying means so the load-applying means can compensate for the inefficiencies of the load-applying means.

By accounting for the friction in the apparatus, and the inefficiencies of the loading devices, a more accurate load can be applied resulting in a more realistic ride simulation.

Another feature of this invention is a device and method to control the heart rate of a person exercising on the exercise apparatus. The heart rate controlling device takes the form of a decreased heart rate means operating when a person's heart rate is below a predetermined lower limit in order to increase the heart rate. The decreased heart rate means determines whether the loads exerted by the variable load means just increased and if so whether the heart rate has been at an increased rate for a predetermined period of time, with the decreased heart rate means causing the variable load means to increase the load if the load is below a predetermined maximum value.

An increased heart rate shutdown means operates when a person's heart rate is more than a predetermined amount above the upper limit, to substantially decrease the load exerted by the variable load means. There is also an increased heart rate means that operates when the person's heart rate is above a predetermined limit in order to decrease the heart rate. The increased heart rate means determines whether the load exerted by the variable load means just increased, and if the load has been at an increased level for a predetermined time, the increased heart rate means causes the variable load means to increase the load. The increased heart rate means decreases the load exerted by the variable load means if the load has not just decreased and if the load is not below a predetermined value.

A means for monitoring the heart rate of the person exercising, and communicating that heart rate to the increased and decreased heart rate means, and to the increased heart rate shutdown means is also provided. A display screen communicates information on the loads and heart rate to the person exercising. If the person exercising does not know the appropriate limits to limit the load means, then the person inputs his or her age and sex, and the limits are determined by a computer.

The steps of the method by which the heart rate of the person exercising is controlled comprise: exercising by use of an exercise device so as to increase the heart rate of the person; varying the load which the exercise device exerts on the person to vary the heart rate of the person; sensing the heart rate of the person during the exercise; increasing the load by a predetermined amount when the person's heart rate is below a first predetermined value, with the increasing step comprising the further steps of: determining whether the variable load applied by the exercise device on the person has just increased, determining whether the variable load has been unchanged for a first predetermined period of time, determining whether the load is below a first predetermined load value, and increasing the variable load by a predetermined amount when the load has not been changed during the first predetermined period of time and when the load is below the first predetermined load value. Additional steps comprise: decreasing the load by a predetermined amount when the person's heart rate is above a second predetermined value, the decreasing step comprising the steps of: determining whether the heart rate is above a third predetermined heart rate value, substantially decreasing the variable load while the heart rate is above the third predetermined load value, determining whether the variable load has just decreased, determining whether the variable load has been unchanged for a second predetermined period of time, determining whether the variable load has reached a second predetermined load value, and decreasing the variable load when the load has not been decreased for the second predetermined period of time and when the variable load has not yet reached the second predetermined load value.

An additional step on this method would be visually displaying messages to the person exercising, regarding either the load exerted by the person in response to the variable load, or to the person's heart rate. The imputing of data on the rider's age and sex, and the calculation of appropriate values or limits on heart rate would be yet another step of this method. Combining the heart controlling method and apparatus with the various variations on the bicycle support provides a realistic ride simulation. As described below, calibrating the friction in the exercise device, and in the load applying device further enhance the accuracy of the control on the load affecting the heart rate. Also as described below, combining the various race simulations provides an advantageous way to train for races without over stressing the physical abilities of the rider. There is thus advantageously provided a means to adjust the load to maintain the user's heart rate within predefined limits, so as to provide a maximum of exercise and training, while automatically monitoring the user's heart rate to prevent over taxing the user.

There is also provided a method and apparatus for realistically simulating the loads experienced during a bicycle race. The race simulation apparatus comprises a stationary bicycle having a rear wheel that can be pedaled; means for selecting the performance ability of a group of simulated racers and simulating the race performance of the selected group of riders; input means connected to the rear bicycle wheel for determining the performance of a person pedaling the bicycle relative to the performance of the simulated racers; display means for displaying the position of the racer with respect to the simulated racers; and variable load means for exerting a variable load on the rear wheel to simulate the loads experienced during racing; and means for varying the load on the bicycle wheel depending on the position of the racer with respect to the group of racers. Preferably the above devices comprise the apparatus previously described above in greater detail.

Preferably the apparatus causes the variable load means to exert an increased load on the wheel to simulate a variable wind load when the racer leaves the group of simulated racers. Further, the preferred apparatus further comprises means for causing the speed of the group of riders to vary randomly during a simulated race.

To simulate various races of selectable difficulty, there is provided a selection means for selecting a performance level of at least one simulated competitor; load calculation means for determining the load exerted by the load-applying means, based on the selected performance level; load sensing means for sensing the load exerted by a rider to overcome the load applied by the load-applying means; means for displaying the performance of a rider relative to the simulated competitors; and means for varying the load exerted by the load-applying means depending on the position of a rider relative to the position of the simulated competitors. As a further variation, the display means further comprises means for displaying the elevation of the selected course, the position of a rider on the preselected course, the position of the rider relative to the simulated competitors, and the total elapsed time the instantaneous speed of the rider, distance traveled, heart rate, and cadence.

Preferably the load applying means takes the form of an electrical load-applying device communicating with a roller for applying variable forces to the roller to simulate the variations in load encountered during actual riding of a bicycle when a rear wheel of a bicycle is frictionally engaged with the roller and has a rear axle supported by the support member, the load-applying device also detecting the power exerted by a rider to overcome the applied load.

The various operations are preferably controlled by a computer controlling the load applied by the load-applying means, the computer having an input device by which a person can select a desired level of competition and the corresponding loads which are exerted by the load-applying device, the computer being programmed to determine and display on the visual display unit the performance of at least one simulated rider of the selected competition level, the computer being programmed to determine and display the position of a rider relative to the position of the simulated riders from the power exerted by the rider and simulated riders, the computer varying the load exerted by the load-applying device depending on the relative position of the rider and simulated riders to simulate wind load. The computer varies the performance of the simulated competitor randomly within the selected level of competition.

The steps in the sequence implemented by the apparatus comprise: applying loads to the rear wheel by an electrical device in order to simulate various riding conditions and situations; applying loads to the rear wheel by a flywheel in order to simulate inertial loads; selecting a race course and the level of difficulty for the competition in the race; determining the loads to be applied to the rear wheel based on the selected level of difficulty for the selected race course; monitoring the performance of a rider pedaling the bicycle with the loads exerted on the rear wheel of the bicycle; displaying the position of the rider relative to at least one simulated rider; and varying the loads on the rider depending on the position of the rider relative to the simulated riders.

Further variations in the sequence comprise randomly varying the performance of the simulated riders during the course of the race; calibrating the electrical device to determine the friction in the exercise device so the electrical device can be adjusted to compensate for the friction loads; determining the efficiency of the electrical device; determining the power output of the electrical device by comparing the efficiency of the electrical device with a second electrical device for which the power output is known; and adjusting the electrical device to account for the frictional losses and the efficiency of the electrical device.

There is thus advantageously provided an apparatus and method not only for simulating the real "feel" of riding a bicycle, but for realistically simulating the loads experienced by riding that bicycle, even accounting for friction and inefficiencies in the apparatus and bicycle. The ability to simulate the environmental loads experienced during races, and to simulate competitors of selectable capability, provides not only a challenge, but a valuable training tool and method. The ability to account for wind loads as a function of the rider's position within a pack provides further realism. The random variation of pack performance during the simulated race allows a rider to experience various strategies of jockeying for position. There is thus provided not only a more realistic and entertaining exercise device, but a device and method highly suitable for training for competitive races.

BRIEF DESCRIPTION OF THE DRAWINGS

The present invention can be more readily understood when reference is made to the accompanying drawings in which:

FIG. 1 is a perspective view of this invention with a bicycle connected to it.

FIG. 2 is a perspective view of this invention with the side covering removed.

FIG. 5 is an exploded perspective of a slidable hinge used on the front fork tube.

FIG. 6 is a perspective view of the assembled hinge shown in FIG. 5.

FIG. 7 is a perspective view of the front fork mounting structure and an adjacent hinge.

FIG. 8 is a perspective view of the invention with its support members folded into adjacent relationship to form a more compact, portable structure.

FIG. 9 is a perspective view of a segment of the invention showing wheels on the structure.

FIG. 10 is a side view of the folded and collapsed structure of FIG. 8.

FIGS. 15a and 15b show a flow chart of a race simulation mode where wind load is taken into account;

DESCRIPTION OF THE PREFERRED EMBODIMENT

Figure 3:
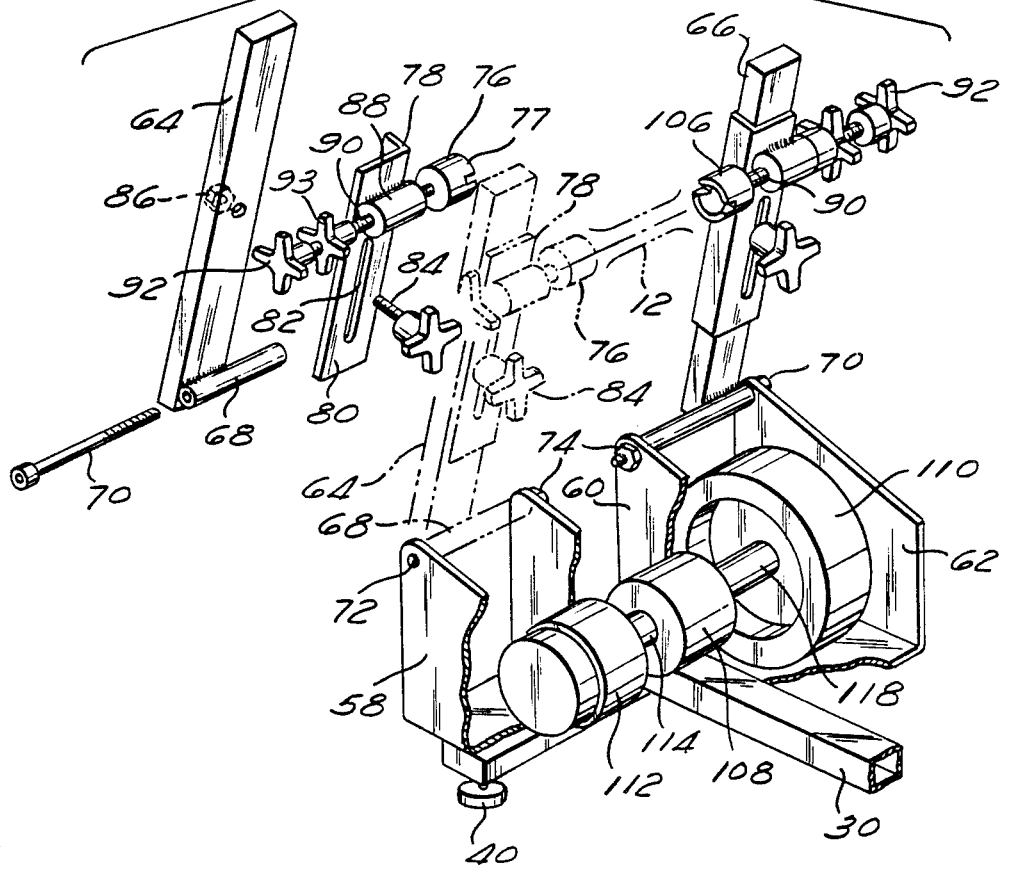
FIG. 3 is an exploded perspective of the rear axle clamp, its support, and the motor and flywheel.

Referring to FIG. 1, there is shown a portion of a multi-speed bicycle having a frame 10 with a rear axle 12 on which is mounted a rear wheel 14 and a rear tire 16. The frame 10 also contains a bottom bracket 18 to which a crank set and pair of pedals 20 are rotatably mounted. A seat 22, handlebars 24 and a rotatably mounted fork 26, are also connected to the frame 10 in a manner known in the art and not described in detail herein.

Referring to FIGS. 1 and 2, a portion of the bicycle is connected to a means for supporting the bike, such as support frame 28. The support frame 28 comprises a bottom member 30 which is approximately 27 inches long, and of a square tubular metal, approximately 1.5 inches per side, with a wall thickness of 0.109 inches.

At one end of the bottom member 30 are two rear legs 32 and 34 (FIG. 9) which extend in opposite directions generally perpendicular to the longitudinal axis of bottom member 30. Preferably, the legs 32 and 34 are opposite ends of a continuous member. At the opposite end of bottom member 30, there are connected two front legs 36 and 38 which extend in generally opposing directions from the bottom member 30. The front legs 36 and 38 extend at an angle of approximately 67 degrees from the longitudinal axis of the bottom member 30 so as to angle away from the rear legs 32 and 34. The same angle, measured from the perpendicular, is 23 degrees. The legs 32 and 34 are all of tubular metal construction having a generally rectangular cross-section approximately 0.75 inch×1.5 inches, with a wall thickness of about 0.120 inches. The legs 36 and 38 are also tubular of construction having a rectangular cross section of about 1 inch×2 inches, and a wall thickness of 0.120 inches.

The bottom member 30 and legs 32, 34, 36 and 38 lie generally in a plane so as to provide a stable support for the bike frame 10 and rider. Support feet 40 are located at the outermost ends of the legs 32-38 and are intended to rest against a floor.

A means for supporting and mounting the front fork 26 of a bicycle is provided which simulates the movement, and flexibility of a front wheel of a bicycle. Thus, fork tube 42 is connected to the juncture of bottom member 30 and front legs 36 and 38. The fork tube 42 extends out of the plane of the legs 32-38 at an angle of approximately 53 degrees from that plane, and in a direction away from the rear legs 32 and 34. The fork tube 42 also extends along a plane passing through the longitudinal axis of the bottom member 30 and oriented substantially perpendicular to the plane formed by the legs 32-38. The fork tube 42 is of a tubular metal construction, using 1.5-inch square tubing with a wall thickness of 0.109 inch.

Referring to FIGS. 2 and 7, a fork mount 44 is connected to the side of the fork tube 42 facing the rear legs 32-34. Referring to FIG. 7, the fork mount 44 comprises a generally rectangular strip of metal 1.25 inches wide by 6.25 inches long and 0.135 inch thick. Two elongated slots 46 and 48 are located along the longitudinal axis of fork mount 44. Preferably, the slots 46 and 48 are approximately 0.34 inch wide by 1.85 inches long, and begin about 0.33 inch from the ends of fork mount 44.

Removable fasteners 50 and 52 extend through the slots 46 and 48 into corresponding apertures (not shown) in the fork tube 42 in order to connect the fork mount 44 to the fork tube 42. Preferably, the fasteners 50 and 52 take the form of threaded bolts. By loosening the fasteners 50 and 52, the slots 46 and 48 allow the fork mount 44 to be slid along the length of the slots 46 and 48, thereby permitting repositioning of the fork mount 44 relative to the length of the fork tube 42. The fasteners 50 and 52 can be removed so the fork mount 44 can be rotated 180 degrees in the plane in which it is mounted, and then re-secured. The fasteners 50 and 52 allow the fork mount 44 to flex, and help simulate a realistic movement of a bicycle attached to the frame 28 via the fork mount 44.

A fork mounting tube 54 (see also FIGS. 1 and 2) is connected to the fork mount 44. The fork mounting tube 54 comprises a metal tube approximately 3.5 inches long, with an outer diameter of about 0.75 inch, and an inner diameter of about 0.38 inch. The interior ends of the fork mounting tube 54 can be threaded. The fork mounting tube 54 is located with its longitudinal axis perpendicular to the longitudinal axis of the fork mount 44 and the slots 46 and 48. The fork mounting tube 54 is not located at the center of fork mount 44, but is offset approximately ½-inch so that it is closer to the end of slot 48 than it is to the end of slot 46.

The fork mount 44 provides an adjustable attachment means for connecting the front fork of a bike to the fork tube 42. The adjustable feature is used to accommodate different sizes of bicycle frames and, as described later, to alter the elevation of the bike frame 10 by repositioning the fork mount 44 on the fork tube 42.

Referring to FIGS. 2 and 3, connected to the rear leg 32 is an inner support plate 56 and an outer support plate 58. The support plates 56 and 58 are substantially parallel plates located in planes substantially parallel to a plane passing through the longitudinal axis of bottom member 30, but substantially perpendicular to the plane in which the legs 32, 34, 36 and 38 are located. The inner support plate 56 is closer to the bottom member 30 than is outer plate 58. The support plates 56 and 58 can be made out of 0.134 inch thick steel.

An inner support plate 60, which generally corresponds to inner support plate 56, is connected in an analogous manner and orientation to rear leg 34. Similarly, an outer support plate 62, which corresponds to outer support plate 58, is connected in an analogous manner and orientation to the rear leg 34.

When a rear wheel 14 and rear tire 16 (FIG. 1) are connected to the apparatus, the rear tire 16 is constrained to move in a predetermined manner. Preferably, a rear axle support member constrains the rear axle 12 of a bicycle to move along a predetermined path. While the support member could be a U-shaped member, preferably, the support member is a pair of axle tubes 64 and 66. The first axle tube 64 is rotatably mounted between the support plates 56 and 58, and a second axle tube 66 is rotatably mounted between the support plates 60 and 62. The first and second axle tubes 64 and 66 are constructed and connected in an analogous manner, so only the first axle tube 64 will be described in detail.

Referring to FIG. 3, the first axle tube 64 is preferably a stiff or rigid member, which does not flex to any great extent, and can comprise a tubular metal bar having a rectangular cross-section approximately 0.75 inch thick and 1.5 inches wide, 12.5 inches long and about 0.12 inch thick. A rotatable mount 68 is connected at one end of first axle tube 64 to one of the 1.5-inch wide sides of axle tube 64. The rotatable mount 68 is shown as a cylindrical tube with an outside diameter of about 1 inch and an inside diameter of about 0.52 inch, and a length of about 4.7 inches which corresponds to the spacing between the support plates 56 and 58. The longitudinal axis of the rotatable mount 68 is perpendicular to the longitudinal axis of the first axle tube 64.

The first axle tube 64 is mounted so that it can pivot in a plane substantially perpendicular to the plane in which the legs 32-38 are located, substantially parallel to the plane of the bottom member 30. This pivot axis is substantially parallel to the rotational axis of the rear wheel 14 and tire 16 connected to the axle tubes 64 and 66.

Pivoting action is achieved by passing a bolt 70 through a hole 72 in the outer support plate 58, through the inside of the rotatable mount 68, and through a corresponding hole (not shown) in inner support plate 56. A fastener 74, such as a threaded nut, is welded to the side of inner support plate 56 so that a threaded end on bolt 70 can be secured by the fastener 74 to prevent inadvertent removal of the bolt 70. The longitudinal axis of the bolt 70 is substantially parallel to the longitudinal axes of rear legs 32 and 34. The bolt 70 thus supports the first axle tube 64 and constrains the axle tube 64 to pivot about the longitudinal axis of bolt 70.

As previously stated, a second axle tube 66 is pivotally mounted and constrained to pivot about a bolt 70 in a similar manner as the first axle tube 64 with such bolts coaxially aligned. The axle tubes 64 and 66 are located adjacent the respective outer support plates 58 and 62. The inner sides of axle tubes 64 and 66 are about 11 inches apart. The first and second axle tubes 64 and 66 thus form movable support means which constrain the rear wheel 14 and tire 16 to move along a predetermined path.

Figure 4:
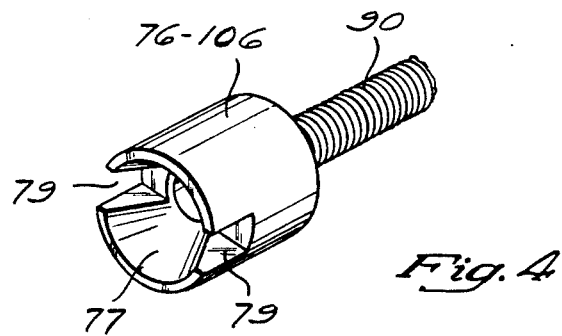
FIG. 4 is a perspective view of a rear axle clamp.

As shown in FIGS. 2 and 3, at the end of axle tubes 64 and 66 opposite the pivotally constrained end are axle clamps 76 and 106 which are connected to the axle tubes 64 and 66 by an axle clamp bracket 78. Referring to FIG. 4, the axle clamp 76 comprises a metal cylinder with a conical depression 77 in one end. A pair of opposing rectangular slots 79 extend partway down opposing sides of the axle clamp 76. In use, a conical-shaped nut or end of the bicycle's rear axle 12 is seated in the conical cavity 77. The slots 79 accommodate D-rings that are used on the quick release skewers used with several bicycle models.

Referring to FIG. 3, the axle clamp bracket 78 comprises a repositionable support plate 80 comprised of a strip of metal having an L-shaped cross-section 0.75 inch on the short side, 1.5 inches on the long side, 6 inches long and 0.120 inches thick. An elongated slot 82 runs along the longitudinal axis of the plate 80 for a length of about 3 inches.

A bolt 84 has a threaded portion which extends through the slot 82 and through a hole (not shown) in axle tube 64. A fastener such as a threaded nut 86 can be removably connected with the threaded end of bolt 84 in order to releasably clamp the plate 80 to the axle tube 64. The plate 80 can be repositioned along the length of the axle tube 64 by loosening the bolt 84 and sliding the plate 80 along the length of slot 82, and then reclamping the bolt 84 and nut 86.

At the end of the plate 80, adjacent the unconstrained end of axle tube 64, is a clamp tube 88. The clamp tube 88 is a cylindrical tube having an outer diameter of about ⅝ inch, a threaded inside diameter of about ½ inch, and a length of about 1.5 inches. The tube 88 has its longitudinal axis substantially perpendicular to the longitudinal axis of axle tube 64 and substantially parallel to the longitudinal axis of bolt 70. A threaded shaft 90 threadingly engages the interior threads of tube 88. The axle clamp 76 is fastened at one end of shaft 90, with a knob 92 being fixed at the opposing end of shaft 90. By rotating the knob 92, the shaft 90 can be rotated so as to reposition the axle clamp 76.

A locking knob 93 is located intermediate to the knob 92 and the tube 88. The locking knob 93 is a knob having a threaded hole through the center, so the knob can be screwed along the length of threaded shaft 90. When the axle clamp 76 is correctly positioned, the locking knob 93 is screwed against the end of tube 88 to provide a frictional lock, preventing axial movement of shaft 90 and axle clamp 76.

A second axle clamp 106 coaxially aligned with clamp 76 (FIGS. 3 and 4) is connected to the unconstrained end of the second axle tube 66 in the same manner as axle clamp 76 is connected to the first axle tube 64. Thus, the details of the second axle clamp 106 and its supporting bracket will not be repeated, other than to note that one axle clamp is slightly longer, with a deeper slot 79, in order to accommodate a variety of designs for axles 12 as used on diverse bicycles.

Referring to FIGS. 2 and 3, a rotatable means helps support the rear wheel 14 of a bicycle connected to the apparatus of this invention. A roller 108 is rotatably supported between the inner support plates 56 and 60. Preferably, the roller 108 is a cylindrical roller with a width of about 2.6 inches and an outer diameter of 2.5 inches, made of aluminum. The roller 108 is rotatably mounted so that its longitudinal axis is substantially parallel with the longitudinal axis of bolt 70 and the pivot axis of first and second axle tubes 76 and 106, and with the rotational axis of a rear wheel 14 connected to the apparatus.

Referring to FIG. 1, preferably the support frame 28 connects to, and supports, the bike frame 10 at three locations. As shown best in FIG. 7, the fork 26 of bike frame 10 can be removably connected to the fork mount 44 by use of a quick-release skewer 110. The quick-release skewer 110 is commonly used on bicycles having a readily removable front wheel, and thus is known in the art and will not be described in detail. The ends of fork 26 fit over the fork mounting tube 54. The quick-release skewer 110 is inserted through the fork 26 and the fork mounting tube 54, and then locked to secure the fork 26 to the fork mount 44. Basically, the fork mount 44 is connected just as if it were the front wheel of a bike.

Referring to FIG. 1, the rear axle 12 of the bike frame 10 is supported by the first and second axle clamps 76 and 106. The conical apertures 77 (FIG. 4) in the axle clamps 76 and 106 fit over the opposite ends of the rear axle 12 so as to support axle 12 and bike frame 10. The rear axle 12 is constrained to move along an arcuate path about the rotational axes of first and second axle tubes 64 and 66, with the path being generally toward roller 108.

The tire 16 rests against the roller 108. Preferably, when viewed in a horizontal plane, the roller 108 is in front of the rear axle 12. The rear axle 12 is shown as being horizontally in front of the rotational axis about which the axle tubes 64 and 66 rotate. Thus, the axle 12 (about which rear wheel 14 rotates) is positioned, relative to a horizontal plane, between the roller 108 and the rotational axis about which axle tubes 64 and 66 rotate. Alternately phrased, if substantially parallel, vertical planes are passed through the rear axle 12, rotational axis of roller 108, and the rotational axes of axle tubes 64 and 66, then the vertical plane containing the rear axle 12 lies between the planes containing the rotational axes of roller 108 and axle tubes 64 and 66. Phases yet another way, a substantially vertical plane through the rear axle 12, would result in the pivot axis of the rear axle tubes 64 and 66 and the roller 108, being located on opposite sides of that vertical plane.

It is believed preferable that the angle of the rear axle tubes 64 and 66, with respect to the vertical, be between 5–30 degrees. From this position, the tubes 64 and 66 will rotate from 1–4 degrees further during operation, depending on rider weight and strength, tire pressure, and the specific bike frame 10. When the bike frame 10 is that of a Schwinn Paramount having a 54 cm frame, and a 99 cm wheelbase, with 700C wheels, the angle is about 26.5 degrees, with the rear axle 12 being about 10.5 inches from the pivot points of axle tubes 64 and 66, and with the rear axle 12 being almost vertically above the rotational axis of roller 108. These dimensions are at the extreme end of dimensions for a short wheelbase racing bicycle.

If the axle 12 is positioned vertically above, or in front of (i.e. toward the handlebars 24) the roller 108, the invention will still function, but as the axle 12 is moved in front of the roller 108, then the performance is increasingly degraded, but it can function. If the rear axle 12 is positioned vertically above, or behind the pivot axis of bolts 70, the rear tire 16 will not be constrained to move into contact with the roller 108 and the apparatus will not satisfactorily function. The objective is to cause the rear tire 16 to move into contact with the roller 108 when the torque on the tire 16 increases, as when the rider leaves the saddle 22 and leans over the handlebars 26 to exert increased force on the pedals 20.

Preferably, the rotational axis of roller 108 is about 4.6 inches (horizontally) from the rotational axis of axle tubes 64 and 66, and about 5.1 inches (vertically) from the rotational axis of axle tubes 64 and 66. The fork mount 44, the axle clamps 76 and 106 (FIG. 2), and the roller 108 provide a three-point support for the bike frame 10 when the frame 10 is coupled to the support apparatus. As a rider pedals the bike via pedals 20, the rear wheel 14 and tire 16 frictionally engage the roller 108, causing roller 108 to rotate.

It is believed possible, although not preferred, to have only the axle clamps 76 and 106 support the bike frame 10, in which case the front fork tube 52 would be eliminated, and the bottom member 30 shortened, so a standard front wheel of a bicycle could be used to support the front fork 26. It is also believed possible, but not preferred, to support the front fork tube 42 separately from the remainder of the frame 28, and to adjust the flexibility of the fork tube 42 to simulate the stiffness, and to allow the movement, of a normal front wheel of a bicycle.

Referring to FIGS. 2 and 3, a variable load device, such as an electromagnetic apparatus like an alternator 112, powered by 110 V AC, is connected to the roller 108. The alternator 112 is connected to the inside support plate 56 and is located between support plates 56 and 58. An alternator shaft 114 (FIG. 3) extends through a hole in the inner support plate 56 (FIG. 2). One end of the alternator shaft 114 (FIG. 3) is connected to the alternator 112, with the opposing end being connected to the roller 108, preferably by shrink-fitting the roller 108 onto the end of the alternator shaft 114.

By applying a variable amount of electrical power to the alternator 112, a variable and controllable amount of resistance can be applied to the roller 108, and thus to the tire 16 and the pedals 20 (FIG. 1). This variable load resistance can be used to simulate the resistance experienced by pedalling on different grades, downhill, flat or uphill. The load can simulate rolling resistance, wind resistance, terrain variations, and if properly programmed, can even simulate the inertia of the bicycle and rider. Thus, the alternator 112 communicates with the roller 108 to simulate a realistic bicycle ride.

Preferably, the inertia is simulated by inertia means, such as a flywheel 116, which is rotatably mounted between the support plates 60 and 62 (FIG. 2). The rotational axis of flywheel 116 coincides with the rotational axis of roller 108 and alternator 112. A specific flywheel could be designed for a given weight of a bicycle and rider, and a maximum speed. Space, safety and weight constraints must also be considered, however. A flywheel 116 found suitable for use is designed to rotate at a maximum speed of about 5000 r.p.m., for an equivalent bike speed of 40 miles per hour for a 27 inch bicycle wheel. Such a flywheel weighs about 22 pounds, and when made of cast iron, can take the form of a rimmed circular disc 2 inches wide and 8 inches in diameter. The inertia of such a usable flywheel has been calculated to be 0.05648 $N*m*sec^2$.

The flywheel 116 communicates with roller 108 so rotation of the roller 108 rotates the flywheel 116. As shown, the flywheel 116 is mounted on a shaft 118 which extends through a hole in the inner support plate 60 to connect to the roller 108. Preferably, the roller 108 is shrink-fit onto one end of the flywheel shaft 118. Thus, the flywheel 116, roller 108 and alternator 112 are essentially on a common rotational shaft. The inertia means, such as flywheel 116, simulates the inertia of a moving bicycle and rider.

Referring to FIGS. 1 and 2, the fork tube 42 is about 21.5 inches long, and contains a hinged joint 124 which is best shown with reference to FIGS. 5 and 6. At a point approximately 7.5 inches above the plane of the legs 32-38 (FIG. 1), the fork tube 42 is cut at an angle such that there is a first end 126 and second end 128 which can be releasably placed in an abutting configuration. On the inside of fork tube 42 adjacent the first end 126, there is inserted a smaller, slidable tubular section 130 which is configured to just fit inside of the first end 126. On opposing sides of slidable tubular section 130 are located longitudinal slots 132. A fastener such as bolt 134 extends through opposing sides of fork tube 42 and through the slots 132 so as to captivate the slidable tubular section 130. Thus, the slidable tubular section 130 can be moved along the longitudinal axis of the fork tube 42 until the bolt 134 bottoms out against the ends of the slots 132.

A rotatable hinge 135 rotatably connects slidable tubular section 130, with a correspondingly sized tubular section 136. The tubular section 136 fits inside of, and is securely fastened to, the second end 128 of fork tube 42.

In operation, the tubular sections 130 and 136 fit on the inside of fork tube 42 and provide a structurally strong joint when the ends 126 and 128 are abutting. The sections 130 and 136 allow the first and second ends 126 and 128 to be separated by a force exerted along the longitudinal axis of fork tube 42. When the first and second ends 126 and 128 are separated, the hinge 135 allows the portion of the fork tube 42 containing the end 128 to be folded so as to collapse the support frame 28 into a more compact configuration (FIGS. 8,10).

In order to ensure the integrity of the hinged joint 124 in the uncollapsed position, and to prevent inadvertent separation of the hinged joint 124, releasable fasteners 138 (FIG. 5) extend through the side walls of fork tube 42 and releasably fasten the slidable tubular section 130 into secure position. The fasteners 138 each comprise a threaded portion 140 extending from a knob 142. Each threaded portion 140 extends through an associated threaded aperture 144 in fork tube 42 so that the end of the threaded portion comes into contact with and binds against the slidable tubular section 130 so as to prevent movement of such sections within tube 42. The apertures 144 preferably are located in the corner of the fork tube 42.

The hinged joint 124, and the rotation of the axle tubes 64 and 66 (FIGS. 8,10), thus provide collapsible joints by which a stable operational structure can be formed, but which can be collapsed or reconfigured to a configuration more suitable for storage or portability.

Referring to FIG. 1, a side cover 120 has one end connected to the support plates 56 (FIG. 2) and 58 with the opposing end connected to the front leg 36. A corresponding side plate 122 is connected between support plates 60 and 62 (FIG. 2), and front leg 38. The side covers 120 and 122 cover the flywheel 116 and alternator 112 (FIG. 2), and provide some stiffness and stability to the support frame 28 as well. Because the support plates 56-62 (FIG. 2) are higher than the front legs 36 and 38, the side covers 120 and 122 slant downward at an angle. The side covers 120 and 122 must be sufficiently low so that a rider's heel will not hit the side plates when pedalling. In a similar manner, the axle tubes 64 and 66 must not be so long that they will be hit by the heel of a rider when pedalling.

The side plates 120 and 122 are removable (see FIG. 2) and comprise generally C-shaped structures preferably made out of sheet metal having a thickness of about 0.060 inches. The sides of the side plates 120 fit over the sides of the support plates 56 and 58 (FIG. 2), and the sides of the side plate 122 fit over the sides of the support plates 60 and 62 (FIG. 2). The sides plates 120 and 122 are spaced apart so that the bottom member 30 is visible between the side plates 120 and 122.

Referring to FIGS. 1 and 2, a display tube 150 is connected to the upper end of fork tube 42. A display 152 is in turn connected to the outer end of display tube 150. The display tube 150 is of the same general construction as fork tube 42, and is rotatably joined to fork tube 42 by rotatable joint 154. The joint 154 comprises a hinged member which uses one or more frictionally releasable devices to hold the joint stable when desired, or to release the joint to allow a rotation when desired. The releasable frictional device is shown as comprising a hinged joint, having a side through which a threaded fastener 156 extends to releasably lock the joint 154 by loosening or tightening the fastener 156, the friction in the joint 154 is increased or decreased, so as to lock the joint 154 into position or to allow it to rotate.

The end of display tube 150 is connected to display 152 by means of a repositionable and tiltable joint 157. A channel bracket 159, having a C-shaped cross section is fastened to the back side of the display 152, with the free legs of the C-section extending outward from the display 152. Each of the free legs of channel bracket 159 has a slot 160, running along the length of the bracket 150. The display tube 150 fits within the channel bracket 159. A releasable fastener 162 has a shaft (not shown) that passes through slots 160 and through a hole (not shown) adjacent the outer end of display tube 150, and connects to a threaded knob (not shown). The fastener 162 and threaded knob cooperate to frictionally lock the end of the display tube 150 to the bracket 159, and thus to the display 152. The connection is releasable by loosening the fastener 162.

The slots 162 allow the display 152 to be positioned relative to the end of the display tube 150, and effectively provide a means for adjusting the height of the display 152. The display 152 can also be rotated about a loosened fastener 162 to adjust the angular orientation of display 152, and tightening the fastener 162 locks the display into position. There is thus provided a joint 157 that allows repositioning and tilting of the display 152.

The display 152 is in electrical communication with the alternator 112 so that various loads can be controlled from, and displayed by, the display 152. The electrical communication mean can comprise wires, which are known in the art and not described in detail, or shown herein. Thus, for example, a rider can input the resistance which is desired to be exerted by the alternator 112, and can monitor the speed at which the bike is being pedalled against that predetermined resistance.

Referring to FIG. 1, the operation of the invention will now be described. A person can take his or her own personal bicycle, remove the front wheel and mount it to the support frame 28. Many modern racing bikes have removable front wheels which facilitate this installation. The fork 26 of the bike frame 10 is attached to the fork mount 44 by use of a quick-release skewer 110. To accommodate for different sizes of bike frames 10, the fork mount 44 can be releasably positioned by loosening fasteners 50 and 52 (FIG. 7), repositioning the fork mounting tube 54 and then refastening fasteners 50 and 52.

Referring to FIG. 7, as previously mentioned, the fork mounting tube 54 is asymmetrically located between the ends of the slots 46 and 48. By slidably positioning the fork mount 44, relative to the fork tube 42, it is possible to adjust the vertical elevation of the bike frame 10. Many riders find a slight uphill elevation to be more comfortable when riding a stationary bicycle.

Preferably the fasteners 50 and 52 are positioned at, and rest against the upper ends of the slots 46 and 48. If so positioned, the mount 44 bears against the fastener 50 and 52.

Since the mounting tube 54 is offset relative to the ends of slots 46 and 48, the mounting plate 44 can be rotated 180 degrees in plane to change the elevation of the mounting tube 54 (and the bike 10), while still allowing the fasteners 50 and 52 to bear against the ends of the slots 46 and 48.

Referring to FIGS. 1 and 3, the tire 16 is placed on the roller 108. The first and second axle tubes 64 are then rotated so the first and second axle clamps 76 and 106 can engage opposite ends of rear axle 12. Turning knobs 92 (FIG. 3) allows the axle clamps 76 and 106 (FIG. 3) to be adjusted along the length of rear axle 12 so the ends of axle 12 can seat in the conical apertures 77. The threaded shaft 90 (FIG. 3) therefore provides an adjustable means for accommodating different axle lengths for positioning of the bicycle frame 10 between the first and second axle tubes 64 and 66. The ability of the first and second axle tubes 64 and 66 to rotate combine with the ability to reposition the axle clamp bracket 78 (FIG. 3) to accommodate a wide range of bike sizes.

Referring to FIG. 1, in operation, the mounting of the fork 26 to the fork mount 44 provides a flexible mount that reduces stresses and fatigue failure problems with the fork 26. The flexibility is provided by the fact that the fork mount 44 can effectively pivot or flexibly rock about a line passing through the fasteners 50 and 52 (FIG. 7), even when those fasteners are tightly secured. The fork mount 44 and the fasteners 50 and 52 bend to allow this flexibility. The flexibility simulates the lateral flexibility of a front wheel of a bicycle to further simulate a realistic ride.

A rider can reposition the fork mount 44 to provide for a level orientation of bike frame 10, or a slightly elevated orientation as previously described. When the rider sits on the seat 22 and exerts force on the pedals 20, the weight of the bicycle and rider force the tire 16 against the roller 108 to provide a frictional drive of the roller 108. The flywheel 116 (FIG. 2) simulates the inertia of the rider and bicycle, while the variable resistance exerted by alternator 112 (FIG. 2) can be used to simulate a ride on a level surface, a downgrade, an uphill grade or any combination of variable grades.

In use, however, the rider does not always stay seated in the seat or saddle 22, but at times of increased power, rises off of the saddle, leans over the handlebars 24 and exerts all of the rider's weight on the pedals 20. Thus, while more of the rider's weight is on the rear wheel when the rider is seated in the saddle 22, the rider's weight is shifted towards the front wheel when the rider rises out of the seat 22 and exerts increased force and weight on the pedals 20.

As the weight of the rider shifts toward the fork 26, the frame 28 operates to maintain, and can actually increase the friction between the tire 16 and the roller 108 in order to prevent slippage. The first and second axle tubes 64 and 66 constrain the rear axle 12 to move along a predefined, arcuate path such that a shift in the weight of the rider toward the fork 26 causes the axle 12, and thus the tire 16, to move toward the roller 108.

It is also believed that the relative stiffness between the bike frame 10 with respect to the frame 28 is such that a movement of the rider toward the fork 26 causes the fork tube 42 to bend or flex forward and downward and, since the bike frame 10 is connected to the fork tube 42, the bike frame 10 causes the constrained axle 12 to rotate toward the roller 108. It is believed preferable that the stiffness of the bike frame 10, including the fork 26, be greater than the stiffness of the support frame 30, which includes fork tube 42, and the axle tubes 64 and 66.

While the exact theoretical basis may not be precisely known, the practical effect is apparent. With the rider seated in the seat 22, the roller 108 and support axles 64 and 66 support the weight that is normally on the rear so there is no excessive friction between the roller 108 and the rear tire 16. As the weight of the rider shifts forward from the seat 22 toward the fork 26, the tire 16 does not slip against the roller 108. The fork tube 42 and constrained rear axle 12 move in unison albeit perhaps in different amounts, with the amount of motion varying with the amount of force exerted on the pedals 20, and the position of the rider relative to the front fork 26. Further, a rider using toe clips and straps on the pedals 20, appears to exert a forward force on the pedals 20 which also causes the fork tube 42 and constrained rear axle 12, to move in unison.

Such was not the case with prior art devices using single or double support rollers. For example, many prior devices used a support that connected to the bottom bracket 18 (FIG. 1). As the weight of the rider shifted forward, the bike pivoted about the support connected to the bottom bracket 18, and the tire 16 moved out of contact with the prior art roller(s). Further, the mere shift in the rider's weight decreased the force on the rear wheel, and thus decreased the friction against the rollers. Thus, the shift of the weight of the rider effectively decreased the friction between the tire and the roller, causing the roller to slip just when the maximum amount of power was being transferred to the tire.

There is thus advantageously provided a means of increasing the friction between the tire 16 and the roller 108 during periods when large amounts of power are being applied to the pedals 20. There is thus also advantageously provided a means of using the location of the weight of the rider to prevent slippage between the tire 16 and the roller 108. There is also provided a means of using the flexibility of the frame 28 to prevent slippage and increase the friction between the tire 16 and roller 108.

Referring to FIGS. 8 and 10, a further advantage of the present invention is that collapsible means are provided so the apparatus can be folded into a compact package to make it readily portable. As previously described, the first and second axle tubes are rotatable about the axis running along the length of bolt 70 (FIG. 3). By correctly positioning the rotational joint, the first and second axle tubes 64 and 66 can be folded into a more compact shape. Preferably, they can be folded adjacent the side covers 120 and 122.

The joints 124, 154 and 157 allow the display 152 to be folded adjacent the side covers 120 and 122. The fork tube 42 and the display tube 150 can fit into the space between the side covers 120 and 122. There is thus provided collapsible means which allow the apparatus to be folded into a more compact, portable configuration than the operational configuration of the apparatus.

Referring to FIG. 2, the heaviest portion of the invention is located at the support plates 56, 58, 60 and 62, which support the flywheel 116 and the alternator 112. Referring to FIG. 9, to increase the ease of portability, a pair of rotatable wheels 170 are mounted at the juncture of the rear legs 32 and 34, opposite the joinder of the bottom member 30. When the invention is lifted so as to rotate about a line passing through the rear legs 32 and 34, the wheels 170 come in contact with the ground or floor so that the invention can be rolled without dragging the foot pads 40. The wheels 170 are not able to roll when the apparatus is in its operational position as shown in FIGS. 1 and 2.

Referring to FIGS. 8–10, preferably, the back surface of the covers 120 and 122 and the support plates 56–62 (FIG. 2) are flat so that the invention can maintain a stable standing position on its end, in a vertical orientation as illustrated in FIGS. 9 and 10.

As previously mentioned regarding FIG. 2, a variable load device such as the alternator 112 is connected so as to rotate in conjunction with the roller 108. As the armature of the alternator 108 rotates, current variations occur which can be used to indicate the rotational speed of the roller 108. The speed can be calculated by measuring the time between pulses from a diode on the alternator. There are six diode pulses for one revolution of the 2.5 inch diameter roller 108. The pulse data can be used to calculate both speed, and distance traveled. The alternator 112 is in electronic communication with the display unit 152 by means such as wires which are known in the art, and not described in detail herein. In practice, the alternator 112 provides two signals to the display unit 112, one for speed, and one for resistor voltage through an external power resistor 243.

The resistor voltage communicates with an analog to digital (A/D) converter in the display 152. The A/D converter is known in the art and is not described in detail herein. The A/D converter assigns a maximum value of 255 to the voltage, which corresponds to a voltage of 25 volts. A resolution of about 0.1 volts in the A/D converter has been found suitable.

Figure 11:
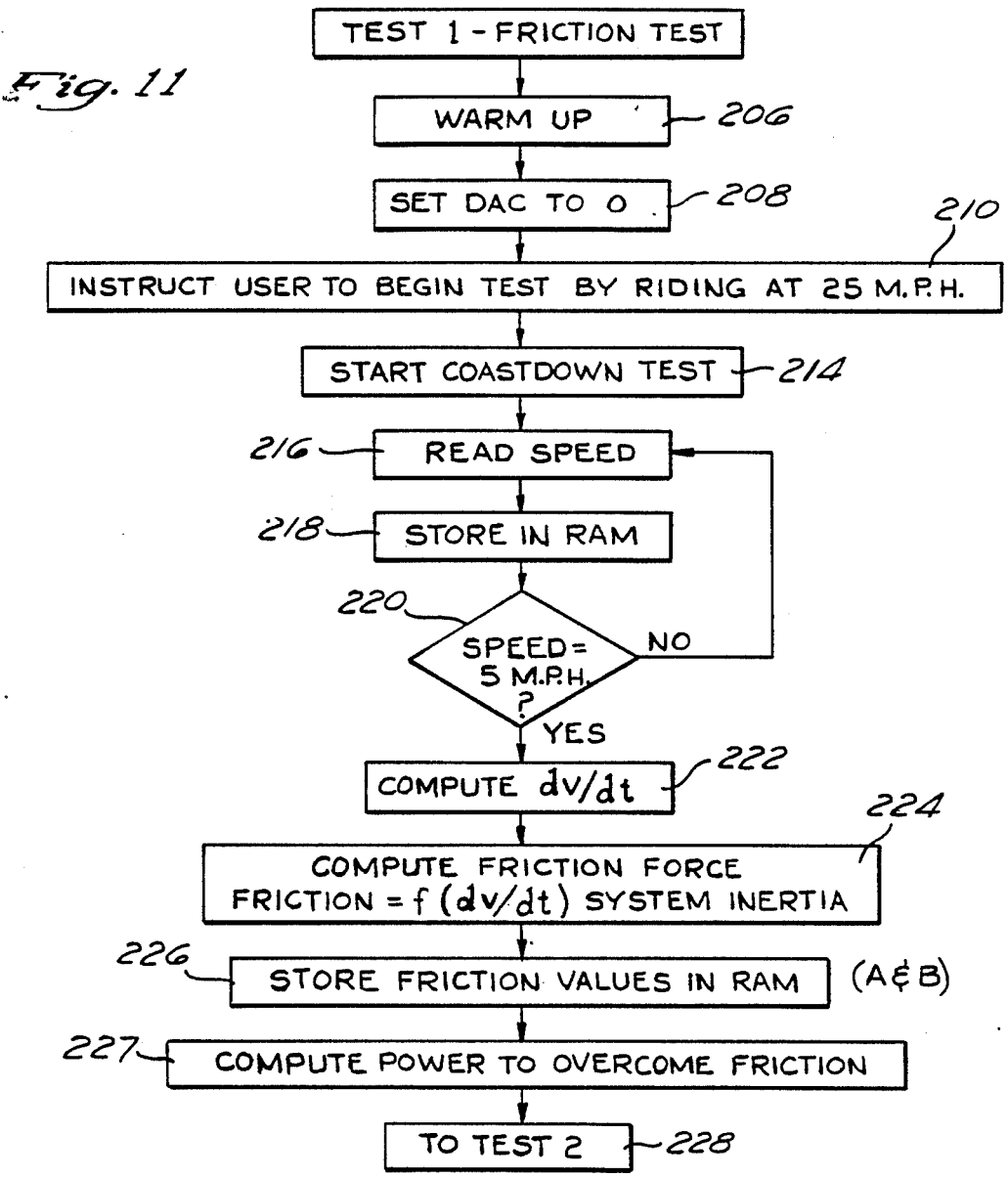
FIG. 11 is a flow chart of a calibration sequence.

Referring to FIG. 11, the display unit 152 contains a computer 200 which monitors and/or calculates the rotational speed of the alternator 112 and the roller 108. The rotational speed of the roller 108 is related to the distance travelled, and the speed of the bicycle, which can be calculated by the computer 200. The computer 200 also controls the voltage to the alternator 112 by means of a digital to analog (DAC) converter, which adjusts the field current in the alternator 112.

The computer 200 also works in conjunction with a timer 202 which monitors various functions of the computer at predetermined intervals. The timer 202 works in conjunction with the computer 200 to calculate the absolute amount of friction in the exercising apparatus, and in the bicycle mounted on the exercise apparatus.

Figure 12:
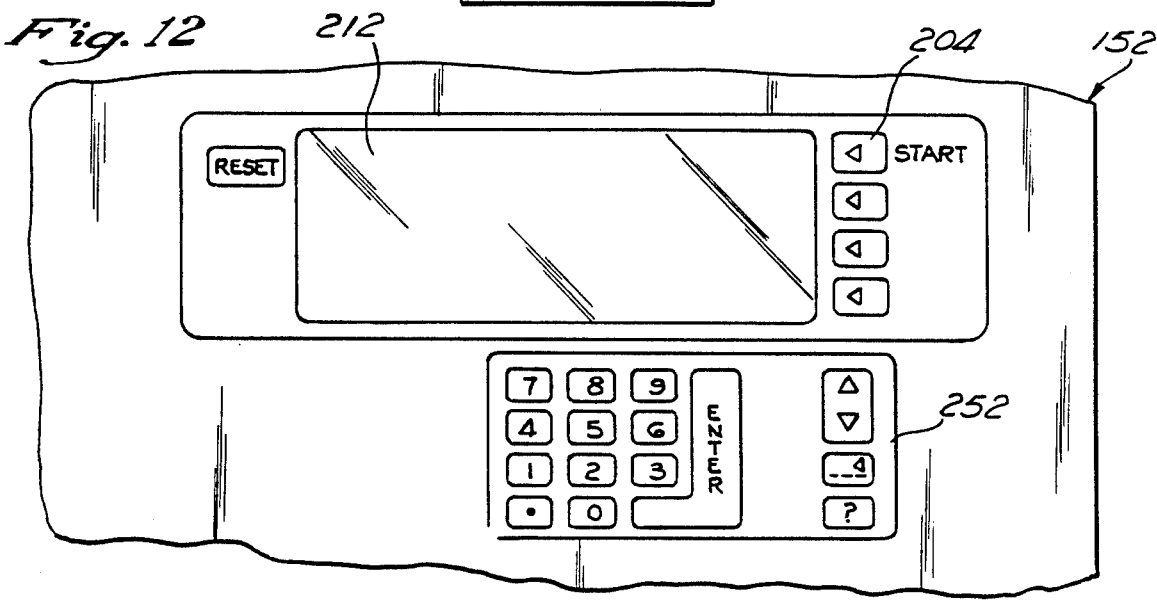
FIG. 12 is a plan view of the display unit as seen from a person exercising on a bicycle placed on the support apparatus shown in FIGS. 1–10.

The flow chart of FIG. 11, taken in conjunction with FIGS. 1 and 12, describes a calibration sequence in which the rider sits on the saddle 22 (FIG. 1) and presses a start button 204 on the display 152 (FIG. 12) in order to initiate the calibration sequence. Upon initiation, block 206 (FIG. 11) instructs the system to warm up, which is preferably achieved by applying full field current to the alternator 112 for about 30 minutes, and then riding the bicycle for a few minutes to disperse the grease in the bearings. The warmup reduces the temperature effects on the system accuracy.

Block 208 initializes the digital to analog converter (DAC) to zero, which causes the alternator 112 (FIG. 2) to place no additional resistance load (other than inherent frictional loads) on the roller 108 (FIG. 2) or tire 16. Block 210 commands the display unit 152 (FIGS. 1 and 12) to display an instruction visible by the user to pedal the bicycle to at least 25 mph. This instruction appears in the display window 212 of display unit 152 (FIG. 12). When the bicycle speed is above 25 mph, an audio signal sounds to indicate that the rider can stop peddling and remain seated on the saddle 22 (FIG. 1). The display window 212 also informs the rider to stop peddling after the audio signal sounds.

Block 214 (FIG. 11) starts the coast down calculation when the speed of the wheel 16 (FIG. 1) reaches a predetermined value, 23 mph in this case. Block 216 reads the speed of the wheel 16 (FIG. 1) while block 218 stores that speed in random access storage (RAM). Decision block 220 compares the speed from block 216 with a predetermined value, preferably 5 mph. If the speed is greater than 5 mph, the decision block returns the sequence to block 216 for re-reading the speed. The speed is checked at periodic intervals, preferably every 0.12 seconds. When the speed reaches 5 mph, the block 222 computes the deceleration of the bicycle dV/dT, where dV is the change in velocity, and dT is the change in time over which the velocity change occurred.

The deceleration is computed by a linear regression, with each consecutive 20 speed readings being averaged to get a series of velocities, $v_1, v_2, v_3, \ldots v_n$ for each velocity v between 5 and 23 mph. A linear regression is then performed on the points:

$$x_i = (v_i + v_{i+1})/2$$

$$y_i = (v_i - v_{i+1})/(20*0.12)$$

Where
$x_i$ = average system velocity (mph)
$y_i$ = system deceleration (mph/sec)

The linear regression gives an equation of the general form:

$$y = A(x) + B$$

which is the deceleration due to friction as a function of velocity. In the general form of the equation, A and B are constants, $x_i$ corresponds to "(x)" and $y_i$ corresponds to "y" which is the acceleration (or deceleration). The angular deceleration can be calculated by multiplying "y" by 14.08 (rad/sec)/mph to get the angular deceleration due to friction as a function of velocity (mph).

Block 224 calculates the frictional resistance in the system in terms of a frictional torque, from the equation:

$$T = Ia$$

Where
T = Frictional Torque of alternator (N*m)
I = Mass moment of inertia (N*m*sec$^2$)
a = angular acceleration (rad/sec$^2$)

The acceleration, or rather deceleration "a" is the value computed by block 222 as a function of velocity. The system inertia is known or can be calculated, and should include the bicycle wheel 14 and tire 16 (FIG. 1). A typical value of the inertia, using a 900 gram wheel, is 0.06296 N*m*sec$^2$. The result calculated by block 224 is the frictional torque of the system under a no load condition. The constants A and B from block 224 are stored in RAM as shown in block 226.

The power to overcome the frictional torque as calculated above can be computed from the equation:

$$P = t*w$$

where
P = Power (watts)
T = Torque (N*m)
w = angular velocity (rad/sec)

Block 227 uses this equation and the above data, with the appropriate conversion factors, to derive the power lost to friction in terms of the linear regression variables A and B:

$$Pf = 11.829*v*[A*v+B]$$

where:
Pf = power lost to friction (watts)
v = bicycle velocity (mph)
A = linear regression constant
B = linear regression constant The power lost to friction, $P_f$, represents the power lost in the system, including frictional power losses from the alternator 112 (FIG. 2). The stator of the alternator 112 (FIG. 2) may have a residual voltage applied, which although small, can cause frictional drag. By knowing the frictional losses of the system, the alternator 112 (FIG. 2) can apply power to the system to simulate road conditions, and to compensate for the frictional losses of the system to increase the realism of the simulation.

The accuracy with which real loads are simulated also depends on how efficient the alternator 112 is in simulating the known loads. If the alternator 112 varies from the standard alternator used in deriving the original equations, applied loads will be less than accurate. To calibrate the alternator 112, the sequence then progresses to test 2, as shown in block 228.

Figure 13:
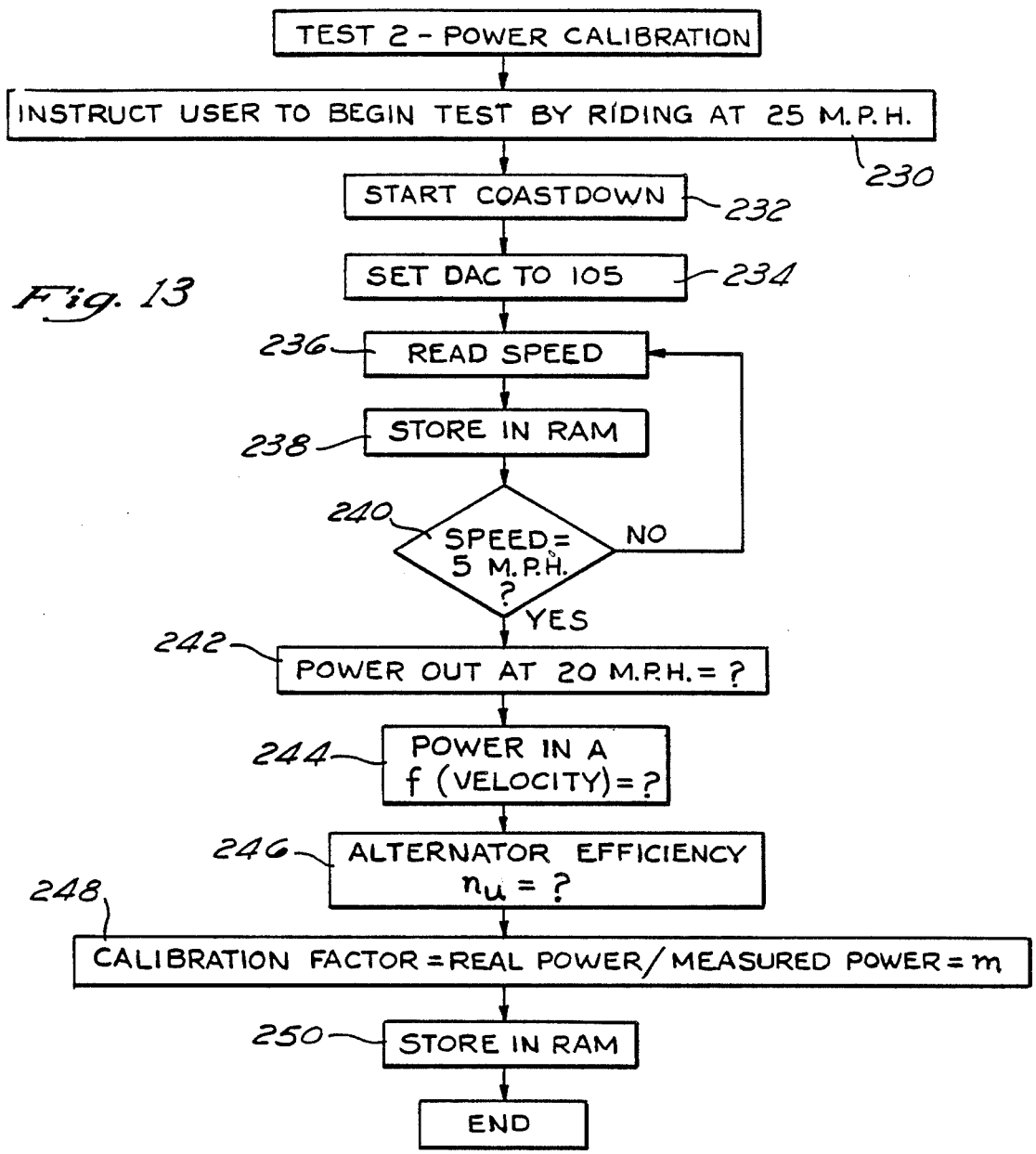
FIG. 13 is a flow chart of a power calibration sequence.

Referring to the flow chart of FIG. 13, the power calibration of the alternator is performed by a second test, which determines the efficiency of the alternator 112 (FIG. 2) with respect to a standard alternator for which the performance characteristics are known, as for example, by measurement on a dynamometer. This standard alternator is used to derive the calibration equation for PA described hereinafter, with $m=1$ in that equation. The comparison with the standard alternator allows compensation for variations in the electrical performance of the alternator 113.

The rider is again instructed to pedal the bike to a predetermined speed (preferably 25 mph) by block 230, which causes a visual message to appear on the display 152 (FIG. 1). An audio signal informs the rider when the predetermined speed is reached. At that point the rider remains seated on the saddle 22 (FIG. 1) while the wheel 14 (FIG. 1) begins to coast to a rest. Block 232 begins the coast down test. Block 234 sets the DAC at a predetermined value, preferably 105. The voltage causes the alternator 112 (FIG. 2) to apply a load to the roller 108 (FIG. 2). A mid range load is preferably used, and the 105 DAC value corresponds to a mid range load of about 20 mph.

Block 236 checks the speed beginning at a predetermined value, preferably 23 mph. Block 238 stores the speed in RAM, along with the voltage at the power resistor 243 in the alternator 112 (FIG. 2). This voltage corresponds to the power out of the alternator 113 (FIG. 2). Decision block 240 checks to see if the speed is below a predetermined value, preferably 15 mph, and if not, it returns to block 236. The loop of blocks 236, 238 and 240 is repeated at periodic intervals, preferably every 0.12 seconds, until the 15 mph value is reached. At that point, several calculations can be made by the computer 200 (FIG. 1).

Block 242 calculates the power dissipated by the alternator 112 (FIG. 2) at a predetermined speed, 20 mph in this case. A regression analysis is performed to determine this value in order to eliminate the possibility of obtaining incorrect information by taking a single power reading at 20 mph. The voltage readings stored in RAM by block 238 are squared, and then a linear regression analysis is performed on the voltage squared as a function of velocity:

$$x_i = v_i$$

$$y_i = (E_i)^2$$

where:
$x_i$ = average system velocity (mph)
$v_i$ = incremental velocity readings (mph)
$y_i$ = system deceleration (mph/sec)
$E_i$ = voltage across power resistor 243 (volts)

The regression analysis results in a linear equation having the general form:

$$y = C(x) + D$$

where
y = a variable that corresponds to $E_2$, the voltage across the power resistor 243, squared (volts)
C = a constant
D = a constant
(x) = a variable corresponding to velocity v (mph)

Thus the immediately preceding equation can be rewritten in the form:

$$E^2 = C*v + D$$

where
E = voltage across power resistor 243 (volts)
v = velocity (mph)
C = a constant
D = a constant A one ohm external power resister 243 (FIG. 2) is connected to the alternator 112 (FIG. 2), and the power dissipated by the external resistor 243 is $E^2$. The power across the external resistor 243 essentially measures the power out of the alternator 113 (FIG. 2). By substituting the velocity of 20 mph the power dissipated at 20 mph can be found.

Block 244 computes the power into the alternator 112 (FIG. 2) as a function of velocity, by performing a linear regression analysis similar to that previously described. This time, however, every 5 speed readings are averaged together to get $v_1, v_2, \ldots v_n$ where the velocity v is between 15 and 23 mph. The regression is performed on the points:

$$x_i = (v_i + v_{i+1})/2$$

$$y_i = [(v_i - v_{n+1})/(5*0.12)] * [(v_i + v_{i+1})/2]$$

where:
$x_i$ = system velocity (mph)
$y_i$ = deceleration times velocity (mph)$^2$/sec The result of this regression is a linear equation, which when multiplied by the proper factors, gives the power into the alternator as a function of velocity:

$$P_i = [F*v + G] * 11.829$$

where:
$P_i$ = power into alternator (watts)
v = velocity (mph)
F = regression constant
G = regression constant Block 246 determines the electrical efficiency of the alternator 112 (FIG. 2) by taking the ratio of the power out, over the power input, at 20 mph.

$$n_u = [(E^2)/(P_{in} - P_f)]_{20 \ mph}$$

where:
$n_u$ = user's alternator efficiency
$E^2$ = alternator output (watts)
$P_{in}$ = alternator input power (watts)
$P_f$ = power lost to friction (watts)

Block 248 determines the calibration factor which gages the performance of a particular user's alternator with the performance of the standard alternator used to derive the foregoing equations. The calibration factor is:

$$m = n_u / n_{cal}$$

where:
m = multiplying factor for alternator
$n_u$ = user electrical efficiency
$n_{cal}$ = calibrated acternator efficiency The calibration factor m is stored in RAM by block 250.

The power a rider puts into the alternator is calculated by knowing the power out of the alternator 112, and the alternator efficiency, as compared to a standard. The voltage is read across the power resistor 243 in the alternator 112 (FIG. 2). The voltage is used to calculate the power exerted by the rider. The power is then multiplied by the calibration factor, m, to compensate for any variations between the user's apparatus, and the standard apparatus.

The display window 212 (FIG. 12) is used to display the power values and associated information for use by the rider. Following the completion of the coast down tests of FIGS. 11 and 13, the information displayed includes the linear regression constants A and B from block 224 (FIG. 11), the calibration factor m from block 248 (FIG. 13). The correlation coefficients for such equations as those of blocks 242 and 244 of FIG. 13 can also be displayed.

A computer source code listing for the calibration steps as described generally in FIGS. 11 and 13 is attached as Appendix A.

The calibration of FIGS. 11 and 13 serves to identify the various factors that can cause the load to vary from what is theoretically predicted. By knowing these variable factors, and calibrating the apparatus to account for these variables or to compensate for frictional losses, the accuracy of the load that is applied is greatly increased, thus giving an increasingly realistic ride simulation. The increased accuracy of the load simulation works in combination with the increased realism provided by the apparatus on which the bike is mounted as described with respect to FIGS. 1-10, in order to provide for a realistic training and exercise apparatus, both as to load exerted, and operational "feel."

Once the apparatus is calibrated, the correct loads must be determined to properly simulate the desired riding conditions. The torque which the alternator 112 presents to the exercise apparatus for the rider to overcome was found to vary linearly with the voltage across the power resistor 243 squared ($E^2$) for one particular speed with the y-intercept equal to zero, where the voltage squared was plotted on the horizontal (x) axis, and the power was plotted on the vertical (y) axis. The slope of these speed or velocity lines was found to be a function of the exponent of the inverse of the speed, as:

$$slope = 0.12832 * e^{(1/v)} - 0.12903$$

where:
v = rider velocity (mph)

Using this information, the equation for $y_i$ from block 222, the equation for nu from block 246, and appropriate conversion factors, the power dissipated by the alternator 112 can be written as:

$$P_A = m[14.08 * v * E^2 * (0.1283\, e^{(1/v)} - 0.12903)]$$

where:
PA = alternator power (watts)
E = power resistor voltage (volts)
v = road speed (mph)
m = calibration factor The computer 200 can accurately simulate the desired environmental loads experienced by a bicycle rider. The appropriate loads are determined as follows, in the preferred embodiment.

The inertia of the bicycle and rider is simulated by the flywheel 116 (FIG. 2), as previously described. The alternator 112 also has some inertia which must be considered. The inertia of a 22 pound flywheel (0.05648 N*m*sec$^2$) when combined with the inertia of the alternator 112 (FIG. 2) has the same inertia as a 113 pound man with a 25 pound bike.

The rolling resistance of the bike is given by the equation:

$$F_R = 4.448 * CR * W$$

Where:
$F_R$ = rolling friction (N)
$C_R$ = coefficient of friction
W = weight of rider and bicycle (lbs)

This equation assumes the bearing friction is accounted for in the coast down tests of FIGS. 11 and 13. A coefficient of friction of 0.004 is preferably used as a median representation of the friction for good clincher tires on a variety of surfaces.

The aerodynamic drag of a bicycle rider is given by the equation:

$$F_D = 0.54 * A * v^2$$

Where:
$F_D$ = air drag (N)
A = frontal area of bicycle and rider (m$_2$)
v = velocity of bicycle (m/sec)

This drag equation assumes a drag coefficient of 0.9, and the standard air density at sea level. The frontal area A changes with rider position and rider size. Assuming that the frontal area varies linearly with rider weight, and a 125 pound rider has a frontal area of 0.306 m$^2$ while a 180 pound rider has a frontal areas of 0.409 m$^2$, and a 25 pound bike with the bike's frontal area included in the preceding figures, then the aerodynamic drag equation becomes:

$$F_D = v^2[(0.00103 * W) + 0.0113]$$

Where:
FD = air drag (N)
v = velocity of bicycle (m/sec)
W = weight of rider and bicycle (lbs)

If the velocity is given in units of mph, then the first and second constants become 0.000206 and 0.00227 respectively. Further variations in the aerodynamic drag equation can be made if it is desired to simulate race conditions such as the position of a rider within a pack of riders. A 30% reduction in air drag is believed to be appropriate for use in the illustrated embodiment if a rider were within a pack of riders.

Assuming a 25 pound bicycle, the load on a bike rider due to inclined or graded surfaces, such as hills, can be calculated as:

$$F_G = 4.448 * G * W$$

Where:
$F_G$ = force due to grade (N)
G = percent grade (e.g. 45% angle 100% grade)
W = weight of rider and bicycle (lbs)

Since power is equal to force times velocity, the power experienced by a bike rider can be obtained by combining the equations for the above forces, to yield the equation:

$$P_r = 0.447 * v * (F_R + F_D + F_G)$$

Where:
$P_r$ = road power for rider (watts)
v = velocity (mph)
$F_R$ = force from rolling resistance (N)
$F_D$ = force from air drag (N)
$F_G$ = force from hills (N)

For given riding conditions from the above equation, the speed for the rider can be calculated, and an appropriate voltage determined to be applied to the alternator 112 in order to simulate that road power. A feedback loop is used in the monitoring and adjustment of the load exerted by the alternator 112. The power a rider is exerting is calculated from the equation:

$$P_{in} = P_A + P_f$$

Where:
$P_{in}$ = rider power exerted by rider (watts)
$P_A$ = alternator power into system (watts)
$P_f$ = friction power (watts)

The computer 200 (FIG. 1) controls and modifies the DAC value, which in turn varies the alternator power $P_A$ as needed to simulate the riding conditions. The DAC value is modified according to the equation:

$$DAC_n = DAC_o \, (P_{in}/P_r)$$

Where:
$DAC_n$ = new DAC value
$DAC_o$ = previous DAC value
$P_{in}$ = rider power in (watts)
$P_r$ = desired rider power in (watts)

Preferably the DACn value is limited to a maximum increase of 40 percent. By using the above load equations and calibration modes, the load experienced by the rider can be varied in a more realistic manner than previously possible.

The computer 200 can be programed to simulate several riding conditions. Referring to FIG. 12, a programming capability is provided whereby the rider can use the keys on the keyboard 252 to select desired loading conditions for specified times and/or speeds. Similarly, the keyboard 252 can be used to recall a stored loading program from the computer 200. One such program is the race mode where the rider competes against other racers simulated by the computer 200.

Figure 14:
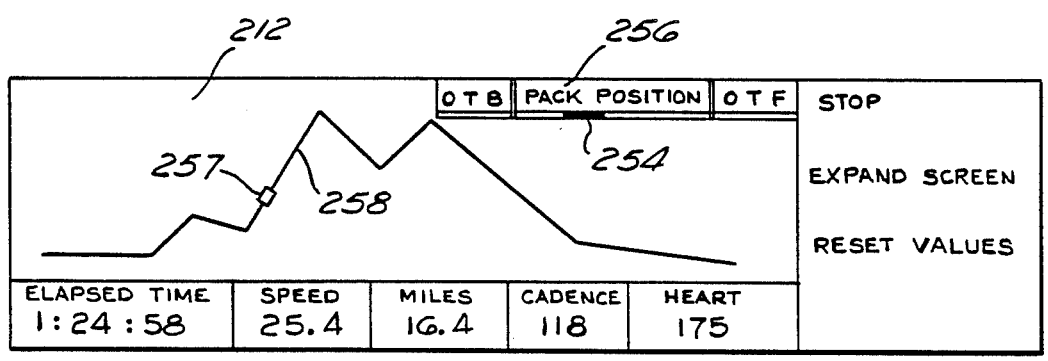
FIG. 14 is a plan view of a display window of the display unit as shown in FIG. 12.

FIG. 14 shows an exemplary display window 212 for the race mode. A first cursor 254 on the display window 212 indicates the position of the rider in a window 256 which displays the pack position so the rider can visualize his/her position with respect to other racers. The window 212 also displays the rider's speed, the elapsed time, the miles traveled, the cadence or pedal rpm, and the rider's heart rate. An elevation profile 258 of the course and the rider's position on the course is also displayed in the window 212. A second cursor 257 indicates the rider's position on the course so the rider can visualize the rider's position with respect to not only the pack via window 256, but also with respect to the overall course and race. The blocks in the window 212 labeled "OTB" and "OTF" allow the first cursor 254 to move within and out of the pack a predetermined extent. "OTB" means "off the back" of the pack, and "OTF" means "off the front" of the pack.

The race mode can use preprogrammed race courses, as for example the course used in the 1984 Olympics. Another preprogrammed course would be a constant incline, sometimes referred to as a fixed grade, where the amount of the incline or grade can be selected by the rider. Alternately, the rider can independently program a course created by the rider. In either event, the computer 200 will control the alternator 112 (FIG. 2) to provide the appropriate loads that simulate the terrain traversed over the length of the course. The rider can select the difficulty of the competition by use of the keyboard 252, in order to compete against riders of varying competence. The greater the competence of the riders, the faster the course would be traversed.

In real races, the riders will bunch up to form a "pack" for much of the race. The pack of riders will progress at varying speeds, sometimes maintaining constant speed, while sometimes increasing speed as riders vie for position. The computer 200 is thus programed to vary the pack speed, preferably in a random manner so the rider can decide whether to alter position as the pack speed varies.

As previously mentioned, the load experienced by a rider can vary depending on the rider's position with respect to the pack since the wind resistance is less for riders in the pack than for those riders who lead or trail the pack. There is thus provided a rider controllable position relative to a pack of simulated riders of a preselected capability, with the rider position relative to the pack varying the wind load experienced by the rider.

Figure 15B:
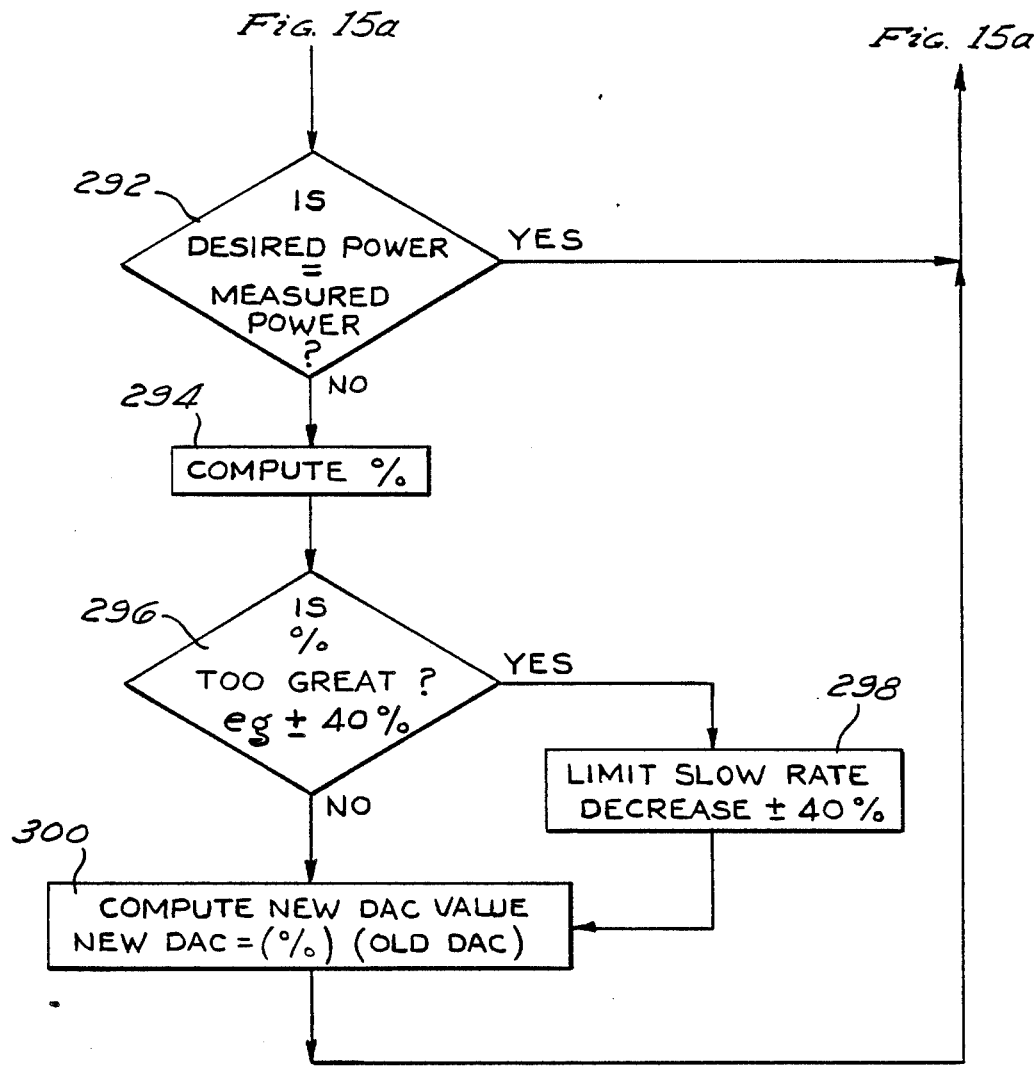

FIG. 15 shows a flow chart of a race mode simulation, while Appendix B contains a computer source code for this simulation and related pack position and power calculations. Block 260 allows the rider to select the level of competition for the race. The more difficult the competition, the greater the loads which must be exerted by the rider on the apparatus in order to keep up with the competition. The loads exerted on the rider by the exercise apparatus, however, are determined by the selected race course as simulated by the alternator 112 (FIG. 2).

The selection of the race course or of the level of competition from the simulated riders is made by using the keyboard 252. Block 262 allows the rider to select the racecourse. A fixed grade may be input, a preprogrammed course can be selected, or a new course can be input by the rider, again by using the keyboard 252 in conjunction with computer algorithms. Block 264 allows the rider's weight to be entered since that affects the load simulation.

Block 266 reads the A/D converter which in turn reads the analog voltage across the external power resistor 243 connected to the alternator 112 (FIG. 2). Block 268 converts that analog voltage to a digital value where the digital value is linear with a maximum of 255. The 255 digital value corresponds to a voltage of 25 volts. Block 270 then computes the appropriate power for the given road simulation according to the formula:

$$P_{total} = P_f + P_A$$

Where:
$P_{total}$ = total power to be overcome by rider (watts)
$P_f$ = power lost to friction (watts)
$P_A$ = alternator power (watts)

The equations for Pf and PA have been previously defined.

Block 272 averages the total power Ptotal over a one second period and displays that power on the display unit 152 (FIG. 1). Block 274 computes the pack power based on the level of experience selected by the rider. Block 276 computes the pack distance to determine the position on the racecourse. Block 278 displays the position of the rider with respect to the pack position, via window 256 (FIG. 14). Block 280 checks the speed of the rider so that block 282 can compute the wind force on the rider, using the previously discussed formula for air drag $F_D$.

Decision block 286 checks to determine if the rider is within the pack, and if so, block 286 reduces the air drag to account for the reduced wind resistance from being in the pack. The reduction is 30% in the described embodiment. Block 288 computes the loads from the grade and rolling resistance, $F_G$ and $F_R$, as previously discussed. Block 290 computes the desired power, $P_r$, as previously described, to be applied to the alternator 112 (FIG. 2) to simulate the above combination of loads.

Once the desired amount of power needed to simulate the riding conditions is determined, decision block 292 checks to see if the desired power is equal to the actual power resistance being exerted on the apparatus by the alternator 112 (FIG. 2) and inherent friction in the system. If the desired power is the same power being applied, no adjustment is necessary and the computer algorithm of FIG. 15 returns to block 266.

If the desired power is not equal to the power being applied, then the program proceeds on to block 294 which computes the percentage ratio of the desired power and applied power. Decision block 296 determines whether this percentage difference is within predetermined limits of acceptability. A 40% difference in the percentage ratio acceptable in the described embodiment. If the percentage difference is beyond the predetermined value, the program proceeds to block 298 where the percentage ratio is adjusted. To prevent sudden surges in load variability, any adjustment of the percentage ratio is limited so as not to exceed a predetermined range, which is plus or minus 40% in the illustrated embodiment. A no decision from block 296 leads to block 300, as does the natural exit from block 298. Block 300 calculates a new DAC value according to the equation:

$$DAC_{new} = (\%)(DAC_{old})$$

Where:
- $DAC_{new}$ = new DAC value (volts)
- $DAC_{old}$ = prior DAC value (volts)
- % = percentage ratio from block 294 or 298.

Following the adjustment of the DAC value, the program returns to block 266 for another iteration. These iterations are repeated at least every second. This computer algorithm allows the rider to train, practice, and experience the exertion required to participate in well recognized courses, in a realistic simulation, and monitor the rider's performance on an absolute time basis, and on a relative basis with respect to a pack of riders having a predetermined ability.

Figure 16:
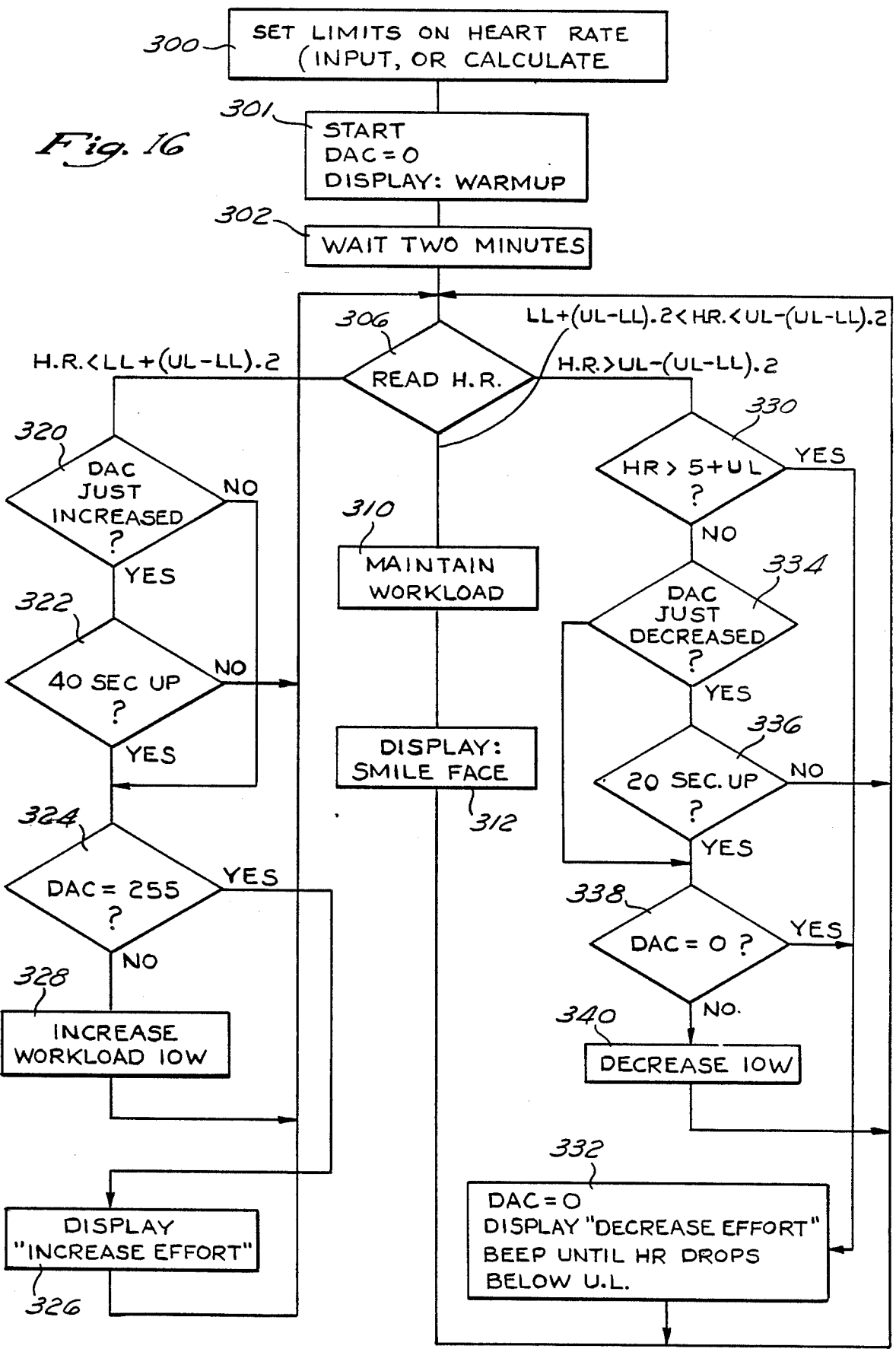
FIG. 16 is a flow chart of a sequence to maintain a rider's heart rate within predetermined limits by varying the load on the exercise apparatus.

Another capability of the apparatus is to monitor the rider's heart rate, and adjust the load experienced by the rider to maintain the heart rate within predetermined limits. A flow chart of a computer program to achieve this purpose is shown in FIG. 16. A copy of a computer source code implementing this flow chart is attached as Appendix C.

The rider initiates the program by keying in the request from keyboard 252 (FIG. 12). Block 300 initiates the program and 226-Arts requests the rider to input information on the upper and lower limits for the heart rate. If no values are input, a default program (not shown) displays a request on window 212 that the rider input the age and sex of the rider, which information is input by keyboard 252. For males, the maximum heart rate is calculated as 220 minus the age. For females, the maximum heart rate is calculated as 226 minus the age. Using this information, limits of 70 to 85% the maximum attainable heart rate during an all out effort are selected from data accessible to computer 200 (FIG. 1).

Block 301 sets the DAC to zero so there is no load exerted by the alternator 112 (FIG. 2), and tells the rider to warm up by a display message in display window 212. As indicated in block 302, the warm up lasts for a predetermined time, two minutes in this case.

Preferably, the rider makes the necessary connections before the warmup period begins so that information on the rider's heart rate can be input into the computer 200 in the display unit 152 (FIG. 1). Various methods known in the art can be used to monitor the rider's heart rate and transmit it to the computer. Preferably, however, the rider wears a chest belt containing a pulse sensor to sense the rider's heart rate. The belt also preferably contains a transmitter so the information can be transmitted to a receiver in the computer 200 in the display unit 152 (FIG. 1). Such devices are known in the art and are not descried in detail herein.

The upper limit (UL) and lower limit (LL) are used in the decision block 306 to determine whether the heart rate (HR) is such that the load exerted on the apparatus by the alternator 112 (FIG. 2) should be increased, decreased, or remain the same. Decision block 306 monitors the heart rate, and if it is within a predetermined range then the load is not altered as indicated in block 310, and the display window displays a signal to indicate all is well, as in block 312, after which the program returns to recheck the heart rate. The predetermined range selected in FIG. 16 is that the heart rate must be greater than:

$$LL + (UL - LL)^*0.2$$

and less than:

$$UL - (UL - LL)^*0.2$$

Where:
- LL = lower limit (from block 306)
- UL = upper limit (from block 306)

Essentially, no consideration is given to changing the load until the heart rate approaches to within 20% of either the upper or lower limits.

If the heart rate was within 20% of the lower heart rate limit, then the algorithm proceeds to decision block 320 which checks to see if the DAC value just recently increased. Since the DAC value affects the load exerted by the alternator 112 (FIG. 2), this step essentially checks to see if the load exerted on the rider has recently increased. If the answer is no, the algorithm proceeds to block 324. If the answer is yes, the algorithm proceeds to block 322 which checks to determine whether the DAC value has been unchanged for more than a predetermined time, 40 seconds in this case. This step is essentially checking to see if the load exerted on the rider has been unchanged for 40 seconds. If the DAC value has not changed for at least 40 seconds, the program returns to block 306 and re-reads the heart rate. If the DAC value has not changed for 40 seconds or more, the program proceeds to decision block 324, which checks to see if the DAC value is at a predetermined level, which in this case is selected as 255. As previously mentioned, 255 is the maximum DAC value, and corresponds to a voltage of 12 volts at the field coil of alternator 112 (FIG. 2). If the DAC value is 255, the program goes to block 326 which displays a request for the rider to increase the effort being exerted, after which it returns to block 306. If the DAC value is below 255, then the program proceeds to block 328 which increases the power by a predetermined amount, which was selected as 10 watts in the preferred embodiment. The program then returns to decision block 306.

If the rider's heart rate is within 20% of the upper heart rate limit, then the program goes to decision block 330 which checks to see if the heart rate has exceeded the upper limit by a predetermined amount, which was selected to be 5 in FIG. 16. If the answer is yes, the heart rate is too high and the program goes to block 332 which sets the DAC to zero to reduce the load, displays a signal on the display unit 152 (FIG. 1) telling the rider to decrease effort, and gives an audio signal (a beep) until the heart rate is lowered to within the pre-specified limits. The program then returns to block 306 to check the heart rate.

If the decision from block 330 is that the rider's heart rate is not greater than the predetermined amount, then the program goes to decision block 334, which checks to see if the DAC was just decreased. If it has just decreased, then the program proceeds to decision block 336 to see how long the heart rate has been heart rate has been above the upper limit. If the DAC has not just decreased, then the algorithm proceeds to block 338.

Block 336 checks to see whether the DAC has changed within the last 20 seconds, and if so the program returns to block 306. If the DAC has been unchanged for 20 seconds or more, then the program proceeds to decision block 338.

Block 338 checks the DAC value, and if it is zero, the program proceeds to block 332 which was previously described. If the DAC value is not zero, then block 340 decreases the power to the alternator 112 (FIG. 2) by a predetermined amount, which is 10 watts in FIG. 16. After decreasing the power, the program returns to block 306.

The algorithm of FIG. 16 thus maintains the load on the exercise apparatus so that the heart rate stays within predetermined limits, and initiates corrective measures as the heart rate approaches those limits. The fast and accurate response of the alternator 112 (FIG. 2) to the load variations allows the loads to be adjusted quickly and accurately enough to maintain the heart rate within the preselected limits. The display unit 152 (FIG. 1) provides visual and audio communication to the rider to further maintain the effectiveness of the system.

When combined with the prior improvements, the method and apparatus for controlling the heart rate allows a racer to optimize the training for a race. The apparatus for supporting the racer's bicycle provides a realistic ride simulation or "feel." The calibration of the friction and alternator efficiency allow the loads to be accurately simulated and to accurately simulate various race conditions. The effects of wind load and pack position can be simulated. The computer and race course selection allows a variety of races to be simulated, so the rider can practice any pre-programmed course, or program independently. The ability to select various levels of competition, and to race against the simulated competition provides race incentive. The random variation of pack performance during a race allows the racer to practice various race strategies. The heart rate monitor allows the racer to track physical performance while having the exercise device take steps to control the load which affects the heart rate.

We claim:

1. A method of calibrating the loads on an exercise device containing a rotating wheel which is rotated by a person exercising with said exercise device and a loading device for applying loads to that wheel, comprising the steps of:
    rotating a wheel in an exercising device until the wheel attains at least a first predetermined rotational velocity;
    allowing the wheel to coast down to a second predetermined rotational velocity during which coasting period the loading device is not exerting loads on the wheel other than inherent frictional loads;
    sensing and recording the time and rotational velocity at periodic intervals as the wheel coasts down from the first velocity to the second velocity;
    determining the rotational mass moment of inertia of any components of the exercise device that rotate because the wheel rotates;
    performing a linear regression analysis on the recorded velocities and times to determine the deceleration of the wheel and rotating components as a function of velocity; and
    deriving the frictional load from rotation of the wheel and the rotating components of the exercise device from the formula Frictional torque equals the Mass Inertia times the Angular deceleration.

2. A method as defined in claim 1, wherein the velocity and time data are taken with the wheel rotating between the speeds of at least 23 miles per hour, and 5 miles per hour, and wherein there are sufficient velocity and time readings that every 20 velocity readings are averaged together to form a series of velocities upon which the linear regression can be performed.

3. A method as defined in claim 1, comprising the further step of:
    computing the power required to overcome the frictional load from the formula: Power equals Torque times angular velocity.

4. A method as defined in claim 1, comprising the further step of:
    determining the efficiency of the loading device;
    determining the power output of the loading device by comparing the efficiency of the loading device with a second loading device for which the power output is known; and
    adjusting the loading device to account for the frictional losses and the efficiency of the loading device.

5. A method as defined in claim 4, wherein the efficiency is determined by performing a linear regression analysis to determine the power dissipated by the loading device at a predetermined speed, and by performing a linear regression analysis to determine the power which the loading device applies to the wheel.

6. A method as defined in claim 4, wherein said loading device comprises an electrical device which exerts a load on the wheel where the load can be varied by varying the voltage applied to the loading device, and wherein the power dissipated is determined by the steps comprising:
    rotating the wheel until the wheel attains at least a third predetermined rotational velocity;
    allowing the wheel to decelerate to a fourth predetermined rotational velocity;
    applying a constant decelerating force from the electrical device in order to further decelerate the wheel as it decelerates from the third to the fourth velocities;
    sensing and recording both the rotational velocity of the wheel and the voltage output by the electrical device at periodic intervals of time as the wheel decelerates from the third velocity to the forth velocity;

performing a linear regression analysis on the recorded wheel velocity and the square of the voltage output from the coast down between the third and fourth velocities to determine the deceleration of the wheel and rotating components as a function of velocity; and wherein the power output by the loading device is further determined by the step comprising:

performing a linear regression analysis on the velocity and on the deceleration times the velocity from the coast down between the third and fourth velocities in order to obtain linear regression constants for use in determining the power applied.

7. A method of accurately and realistically simulating environmental loads in a stationary exercise apparatus, comprising the steps of:

mounting a bicycle in a support apparatus so a rear tire of the bicycle rides against at least one roller;

connecting a loading device to the exercise apparatus so the loading apparatus can exert a controllable load on the rear tire;

pedaling the bicycle until the rear tire reaches a firs rotational velocity;

letting the rear tire coast down to a second predetermined velocity while the loading device exerts no loads other than its inherent frictional loads;

sensing and recording the velocity of the rear tire at periodic time intervals as the tire coasts from the first velocity to the second velocity;

determining the rotational mass moment of inertia of any components tire bicycle and support apparatus that rotate with the tire during the coast down period;

performing a linear regression analysis on the recorded velocities and times to determine the deceleration of the rear tire and rotating components as a function of velocity; and deriving the frictional load from rotation of the tire and the rotating components from the formula: Frictional torque equals the Mass Inertia times the Angular deceleration.

8. A method as defined in claim 7, further comprising the steps of:

determining the efficiency of the loading device;

determining the power output of the loading device by comparing the efficiency of the loading device with a second loading device for which the power output is known; and adjusting the loading device to account for the frictional losses and the efficiency of the loading device.

9. A method as defined in claim 8, wherein the linear regression step comprises:

performing a linear regression analysis on the recorded times and velocities between a third velocity and the second velocity to determine the deceleration of the rear tire and rotating components as a function of velocity, where the third velocity is between the first and second velocities.

10. A method as defined in claim 9, further comprising the step of:

connecting a flywheel to the support apparatus so the rear tire causes the flywheel to rotate and simulate the inertia of a rider and bicycle, and where the mass moment of inertia includes the inertia of the flywheel.

11. A method as defined in claim 10, wherein the loading device comprises an alternator which can exert a controllable load on the rear tire by controllably varying the voltage applied to the alternator, and wherein the efficiency of the alternator is determined by determining the power dissipated by the alternator and the power output by the alternator, the power being dissipated being determined by comprising the steps of:

rotating the tire until the tire attains a fourth predetermined rotational velocity;

allowing the tire to decelerate to a fifth predetermined rotational velocity;

applying a constant decelerating force from the alternator in order to further decelerate the tire as it decelerates from the fourth to the fifth velocity;

sensing and recording the rotational velocity of the wheel and the voltage output by the electrical device at periodic intervals as the tire decelerates from the fourth velocity to the fifth velocity;

performing a linear regression analysis on the recorded tire velocity and the square of the voltage to determine the deceleration of the tire and rotating components as a function of velocity; and wherein the power output by the alternator is determined by the steps comprising:

performing a linear regression analysis on the velocity and on the deceleration times the velocity in order to obtain linear regression constants for use in determining the power applied.

* * * * *

UNITED STATES PATENT AND TRADEMARK OFFICE
CERTIFICATE OF CORRECTION

PATENT NO. : 4,938,475

DATED : July 3, 1990

INVENTOR(S) : Bruce A. Sargeant, Mark J. Hoffenberg, Rob Reasons, Robert A. Walpert It is certified that error appears in the above-identified patent and that said Letters Patent is hereby corrected as shown below:

Title page, add --Assignee: Schwinn Bicycle Company, Chicago, Illinois--.

Column 22, line 27, change "P = t * w" to --P = T * w--.

Column 22, line 38, change "Pf" to --$P_f$--.

Column 22, line 41, change "Pf" to --$P_f$--.

Column 23, line 1, change "PA" to --$P_A$--.

Column 24, line 57, change "acternator" to --alternator--.

Column 25, line 43, change "nu" to --$n_u$--.

Column 25, line 47, change "012903" to --0.12903--.

Column 25, line 50, change "PA" to --$P_A$--.

Column 25, line 68, change "CR" to --$C_R$--.

Column 26, line 33, change "FD" to --$F_D$--.

Column 26, line 52, change "45% angle 100% grade" to --45% angle = 100% grade--.

Column 26, line 58, change "FG" to --$F_G$--.

Column 27, line 24, change "DACn" to --$DAC_n$--.

Column 28, line 54, change "Pf and PA" to --$P_f$ and $P_A$--.

Column 28, line 56, change "Ptotal" to --$P_{total}$--.

Column 32, line 37, change "step" to --steps--.

Column 33, line 1, change "forth" to --fourth--.

Column 33, line 26, change "firs" to --first predetermined--.

UNITED STATES PATENT AND TRADEMARK OFFICE
CERTIFICATE OF CORRECTION

PATENT NO. : 4,938,475

DATED : July 3, 1990

INVENTOR(S) : Bruce A. Sargeant, Mark J. Hoffenberg, Rob Reasons, Robert A. Walpert It is certified that error appears in the above-identified patent and that said Letters Patent is hereby corrected as shown below:

Column 33, line 35, change "tire bicycle" to --of the bicycle--.

Column 34, line 37, change "wheel" to --tire--.

Column 34, line 46, change "steps" to --step--.

Signed and Sealed this

Seventeenth Day of March, 1992

*Attest:*

HARRY F. MANBECK, JR.

*Attesting Officer*   *Commissioner of Patents and Trademarks*